US011911073B2

United States Patent
Erekovcanski et al.

(10) Patent No.: US 11,911,073 B2
(45) Date of Patent: *Feb. 27, 2024

(54) BIOSENSOR INSERTER APPARATUS AND METHODS

(71) Applicant: Ascensia Diabetes Care Holdings AG, Basel (CH)

(72) Inventors: Nicholas Erekovcanski, Butler, NJ (US); Eugene R. Prais, West Milford, NJ (US); Thomas A. J. Mayer, Jr., Glenmoore, PA (US); Cameron M. Young, Tarrytown, NY (US)

(73) Assignee: Ascensia Diabetes Care Holdings AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/166,155

(22) Filed: Feb. 8, 2023

(65) Prior Publication Data

US 2023/0181218 A1   Jun. 15, 2023

Related U.S. Application Data

(63) Continuation of application No. 16/984,125, filed on Aug. 3, 2020, now Pat. No. 11,602,373.

(Continued)

(51) Int. Cl.
| | | |
|---|---|---|
| *A61B 17/34* | (2006.01) | |
| *A61B 5/145* | (2006.01) | |
| *A61B 5/00* | (2006.01) | |

(52) U.S. Cl.
CPC ...... *A61B 17/3468* (2013.01); *A61B 5/14532* (2013.01); *A61B 5/6847* (2013.01); *A61B 17/3496* (2013.01)

(58) Field of Classification Search
CPC ............ A61B 5/15115; A61B 5/15117; A61B 5/150412; A61B 5/12029; A61B 5/1519;
(Continued)

(56) References Cited

U.S. PATENT DOCUMENTS

2017/0188912 A1* 7/2017 Halac ..................... A61B 5/688

FOREIGN PATENT DOCUMENTS

EP        2826422 A1    10/2021

OTHER PUBLICATIONS

Taiwan Patent Application Official Letter and Search Report dated Dec. 12, 2023.

* cited by examiner

*Primary Examiner* — Majid Jamialahmadi
(74) *Attorney, Agent, or Firm* — Erise IP, P.A.

(57) ABSTRACT

A biosensor inserter includes a push member with a push element, a contact member including a latch, a transmitter carrier supporting a transmitter and sensor assembly, and a pivot member having a latch end, the pivot member supporting an insertion device during biosensor insertion. In operation, the push member is telescoped axially by the user relative to the contact member, which is provided in contact with a user's skin. This pushes the push element against the pivot member and translates the transmitter carrier during insertion of the biosensor. During a first portion of a stroke of the insertion device, insertion of the biosensor is accomplished, and the pivot member is prevented from pivoting. In a second portion of the stroke, after latch end moves past the latch, the pivot member is allowed to pivot and the insertion device is retracted. Other system and method embodiments are provided.

20 Claims, 25 Drawing Sheets

Related U.S. Application Data

(60) Provisional application No. 63/027,346, filed on May 19, 2020, provisional application No. 62/889,444, filed on Aug. 20, 2019.

(58) Field of Classification Search
CPC ............ A61B 5/15029; A61B 5/15113; A61B 5/15194; A61B 5/15128; A61B 17/3468; A61B 17/3496; A61B 2560/063
See application file for complete search history.

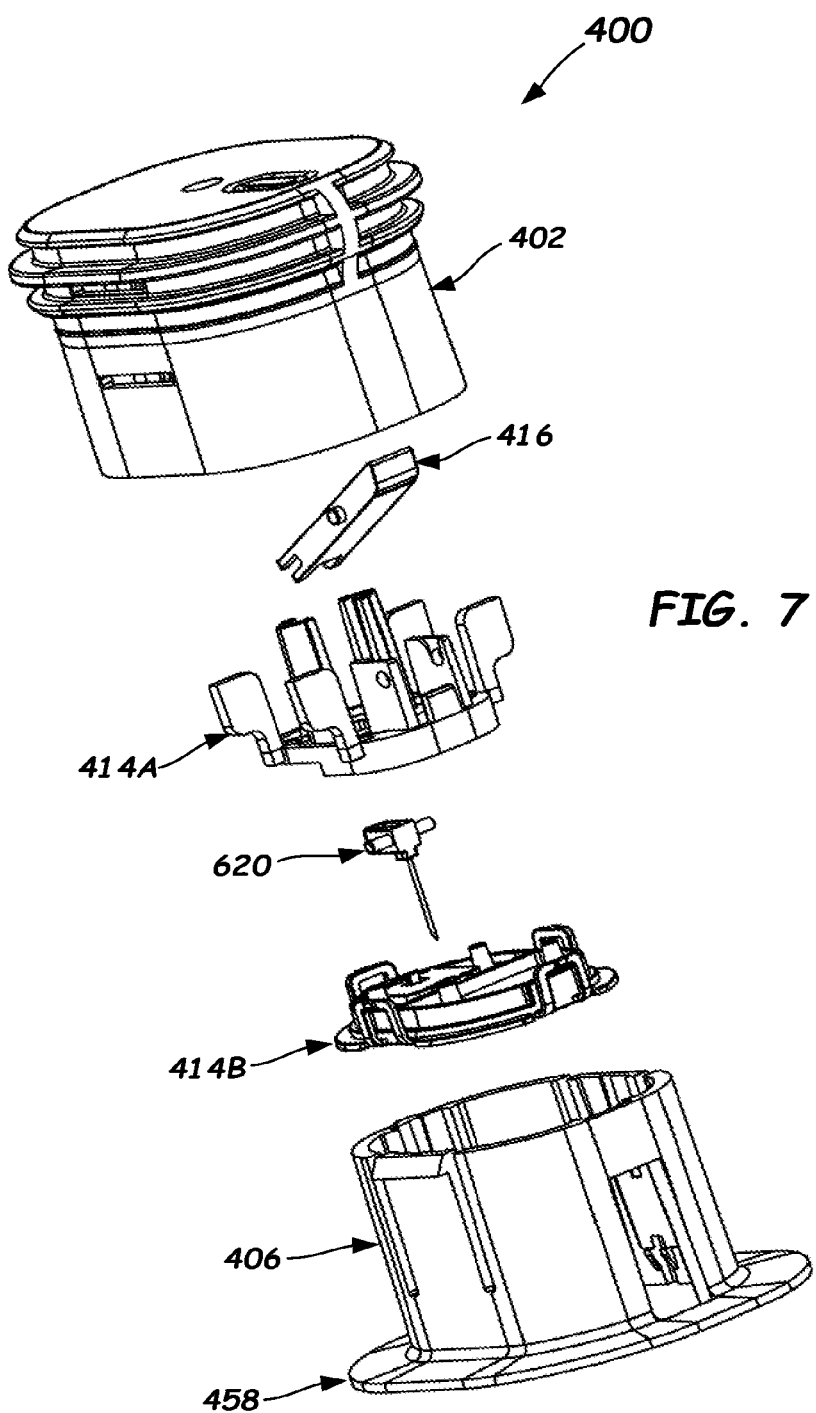

BIOSENSOR INSERTER APPARATUS AND METHODS

CROSS-REFERENCE TO RELATED APPLICATIONS

This patent application is a continuation application claiming priority benefit, with regard to all common subject matter, of U.S. patent application Ser. No. 16/984,125, filed Aug. 3, 2020, and entitled "BIOSENSOR INSERTER APPARATUS AND METHODS" ("the '125 Application"). The '125 Application claims priority to U.S. Provisional Application No. 63/027,346, filed May 19, 2020, and entitled "BIOSENSOR INSERTER APPARATUS AND METHODS," and U.S. Provisional Application No. 62/889,444, filed Aug. 20, 2019, and entitled "CONTINUOUS GLUCOSE MONITOR INSERTER APPARATUS AND METHODS." The identified earlier-filed applications are hereby incorporated by reference in their entirety into the present application.

FIELD

The present disclosure relates to an inserter configured to insert a biosensor, which can be part of a continuous glucose monitor (CGM).

BACKGROUND

Continuous analyte sensing, such as with a continuous glucose monitor (CGM), has become a routine sensing operation, particularly in diabetes care. By providing real-time glucose monitoring that provides glucose concentrations over time, therapeutic actions, such as insulin introduction, may be applied in a timely manner and the glycemic condition may be better controlled.

During a CGM operation, a biosensor of a transmitter and sensor assembly is inserted subcutaneously and continuously operated in an environment surrounded by tissue and interstitial fluid (ISF). The biosensor inserted under the skin provides a signal to a transmitter of the transmitter and sensor assembly, and that signal can be indicative of the patient's blood glucose level. These measurements may be made intermittently and automatically many times throughout the day (e.g., every few minutes or at some other suitable interval).

The transmitter of the transmitter and sensor assembly is adhered to the outer surface of a user's skin, such as on the abdomen, on the back of the upper arm, or at another suitable location, while the biosensor is inserted through the skin so as to contact ISF. This skin insertion process may be referred to as "insertion." Devices for carrying out this insertion may be referred to as "inserters."

Inserter designs may be complicated and costly to manufacture. Accordingly, improved designs of inserter apparatus and methods of operating them are desired.

SUMMARY

In some embodiments, a biosensor inserter includes a push member including a push element, a contact member translatable relative to the push member, the contact member including a latch, a transmitter carrier translatable relative to the contact member and configured to support a transmitter and sensor assembly during insertion of a biosensor, a pivot member configured to pivot on the transmitter carrier, the pivot member including a latch end, and an insertion device drivable by the pivot member to insert the biosensor, wherein during insertion of the biosensor in a first portion of a stroke, the pivot member is prevented from pivoting, and wherein when the latch end of the pivot member moves past the latch, the pivot member is allowed to pivot in a second portion of the stroke and retract the insertion device.

In further embodiments, a biosensor inserter configured to insert a biosensor of a continuous monitoring transmitter and sensor assembly is provided. The biosensor inserter includes a push member having a rigid push element and a first alignment feature; a contact member having a latch and a second alignment feature, the contact member configured to telescope within the push member; a transmitter carrier configured to support the continuous monitoring transmitter and sensor assembly during insertion of a biosensor; a pivot member configured to pivot relative to the transmitter carrier, the pivot member including a latch end, and an insertion device supported by the pivot member; and wherein the first alignment feature of the push member is configured to interface with the second alignment feature of the contact member so as to align the latch end with the latch, and wherein the pivot member is configured to slide relative to an internal guide feature of the contact member and the pivot member is prevented from pivoting in a first portion of a stroke during insertion of the biosensor, and wherein when the latch end of the pivot member moves past the latch, the pivot member is allowed to pivot in a second portion of the stroke and retract the insertion device leaving the biosensor implanted.

In further embodiments, a method of using an inserter apparatus to insert a biosensor is provided. The method includes providing the biosensor inserter comprising: a push member including a push element, a contact member translatable relative to the push member, the contact member including a latch, a transmitter carrier translatable relative to the contact member and configured to support a transmitter and sensor assembly during insertion of the biosensor, a pivot member configured to pivot on the transmitter carrier, the pivot member including a latch end, and an insertion device drivable by the pivot member; contacting the contact member to a user's skin; pushing on the push member during a first portion of a stroke to cause the push element to contact the pivot member, translate the transmitter carrier, and insert the insertion device and biosensor through and into the user's skin, wherein the pivot member is prevented from pivoting during the first portion of the stroke; and continuing to push the push member until delatching of the latch end from the latch, wherein the pivot member is allowed to pivot during a second portion of the stroke and retract the insertion device while leaving the biosensor implanted.

Other features, aspects, and advantages of embodiments in accordance with the present disclosure will become more fully apparent from the following detailed description, the claims, and the accompanying drawings by illustrating a number of example embodiments. Various embodiments in accordance with the present disclosure may also be capable of other and different applications, and its several details may be modified in various respects, all without departing from the scope of the claims and their equivalents. Thus, the description is to be regarded as illustrative in nature, and not as restrictive.

BRIEF DESCRIPTION OF THE DRAWINGS

The drawings are to be regarded as illustrative in nature, and not as restrictive. The drawings are not necessarily drawn to scale. Like numerals are used throughout the drawing to denote like elements.

FIG. 7 is an exploded front perspective view of an alternative embodiment of biosensor inserter in accordance with the disclosure.

DETAILED DESCRIPTION

In one or more embodiments described herein, a biosensor inserter is provided that may be inexpensively manufactured. The biosensor inserter is configured to implant (insert) a biosensor into the skin of a person. For example, in some embodiments, the biosensor inserter may include a transmitter carrier that holds a transmitter and sensor assembly during insertion of the biosensor, and a push element that translates the transmitter carrier toward a user's skin during a first portion of a stroke of the biosensor inserter. In one or more embodiments, the push element may be formed from a rigid piece of material, which may be integral with or rigidly coupled to the push member. The push element may be offset from a central axis of the biosensor inserter.

In some embodiments, a pivot member, which contacts and operatively drives an insertion device of the biosensor inserter, is restrained from pivoting as the transmitter carrier translates toward a user's skin during a first portion (insertion portion) of the stroke of the biosensor inserter, but is allowed to pivot once de-latched after the biosensor is implanted in a user's skin. Once delatched, the pivot member may pivot in a second portion of the stroke of the biosensor inserter, which causes the retraction (retraction portion) of the insertion device and leaves the biosensor inserted into the user's skin. Thus, the pivot member does not pivot in the first portion of the stroke.

These and other structural and functional features of embodiments of the inserter are described below with reference to FIGS. 1A-7.

Figure 1A:
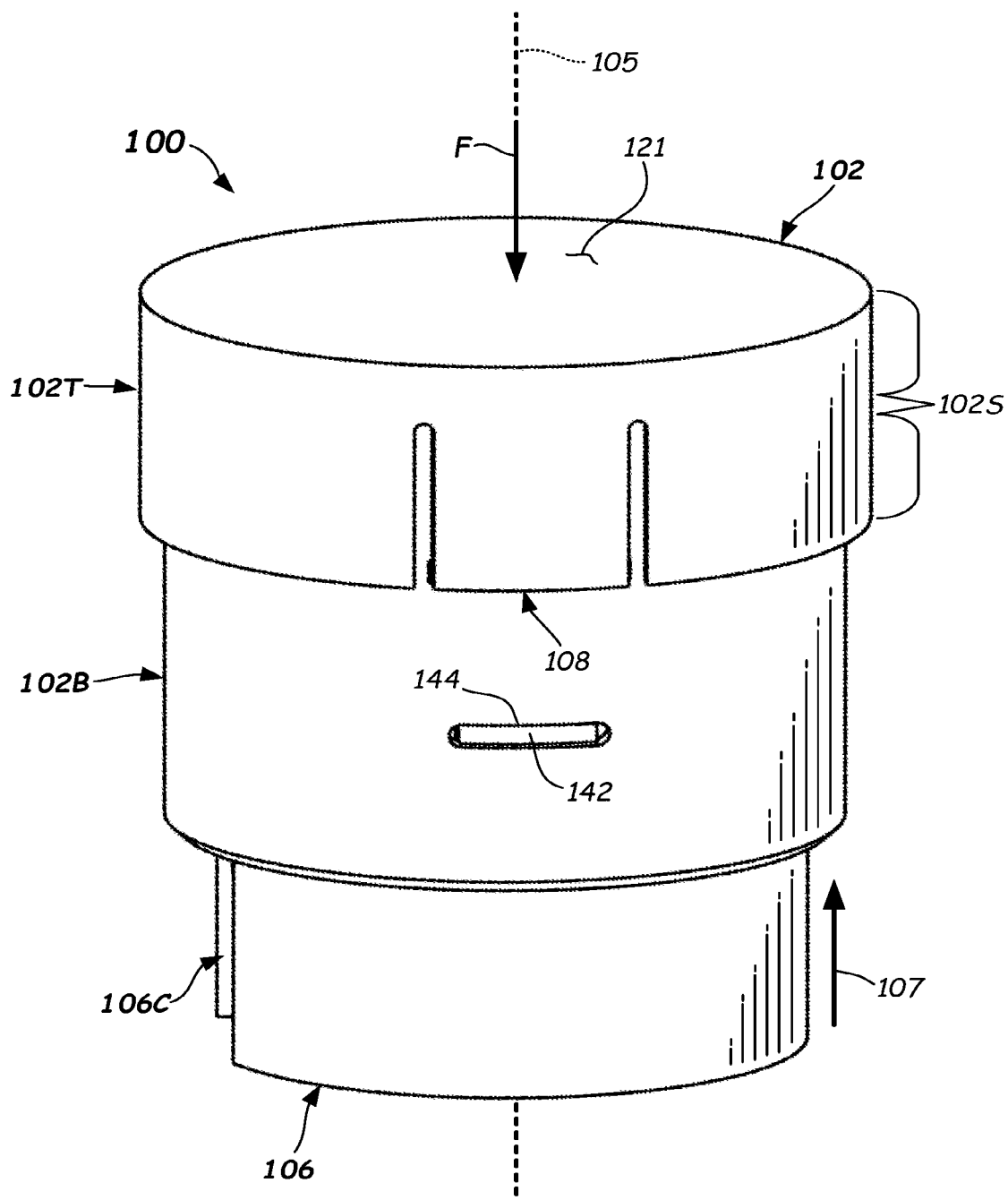
FIG. 1A is a side-perspective view of a biosensor inserter in accordance with one or more embodiments provided herein.
Figure 1B:
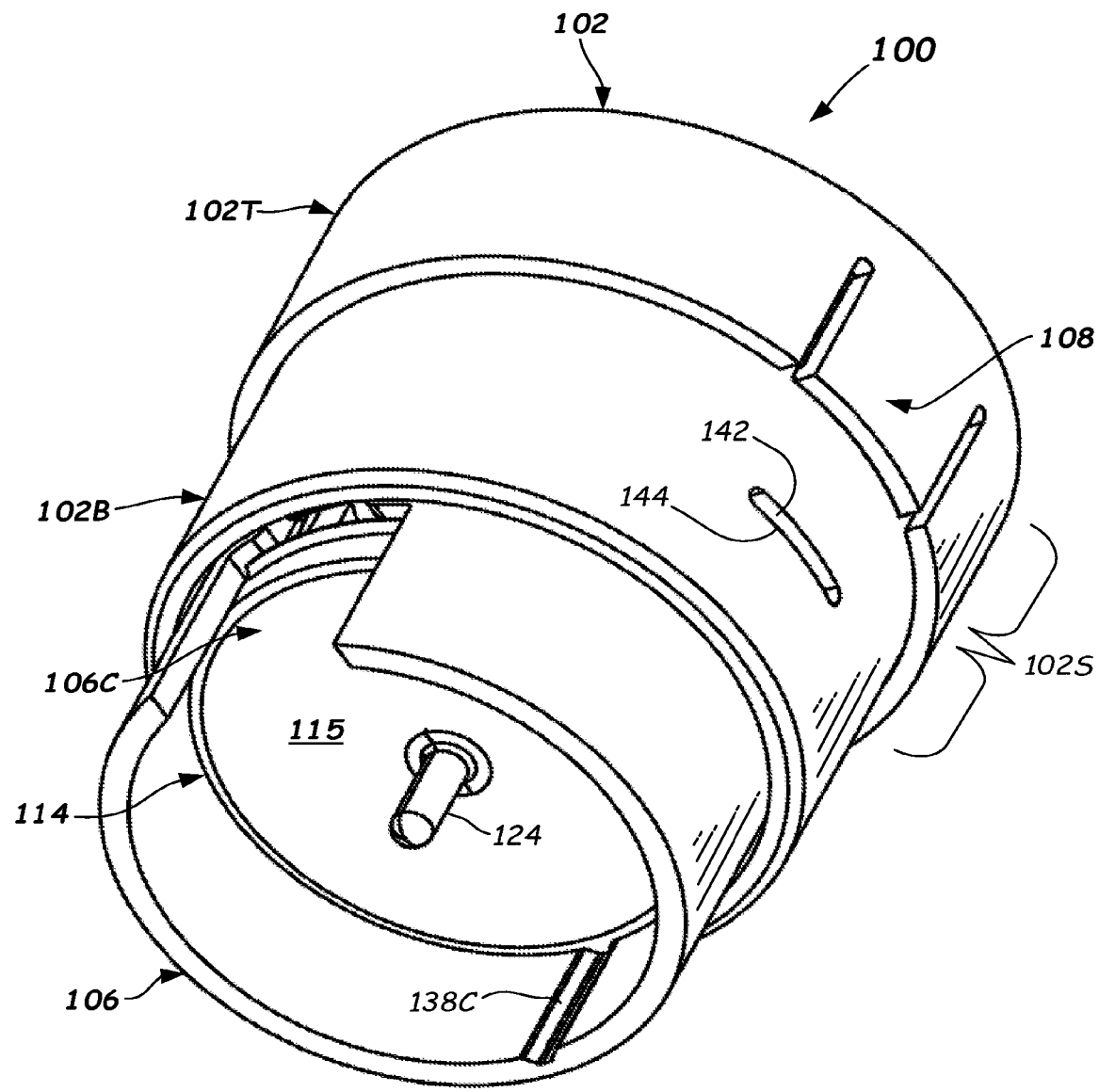
FIG. 1B is an underside-perspective view of a biosensor inserter including a needle cover in accordance with one or more embodiments provided herein.
Figure 1C:
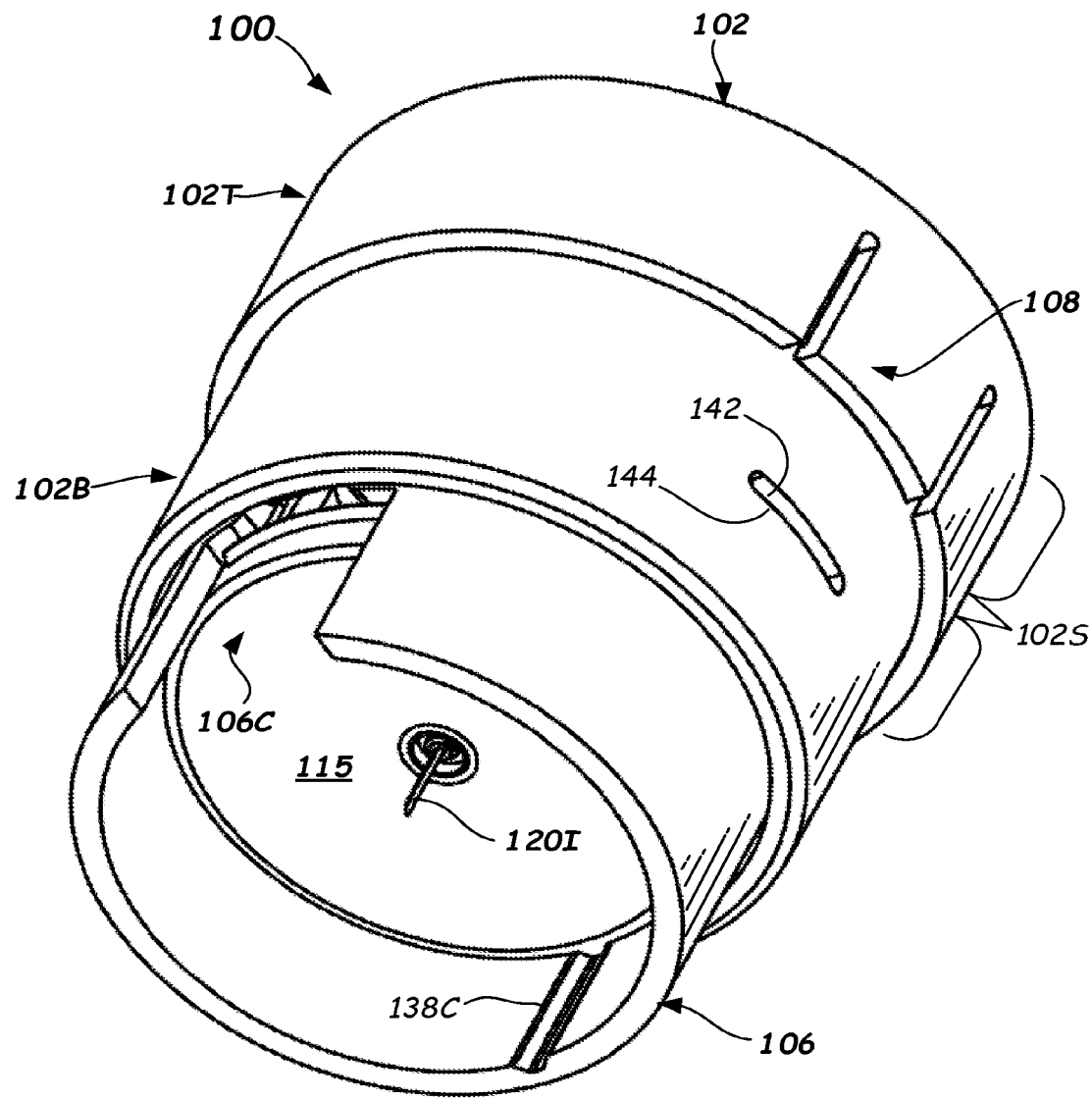
FIG. 1C is an underside-perspective view of a biosensor inserter with the needle cover removed exposing the inserter portion of the insertion device in accordance with one or more embodiments provided herein.

FIGS. 1A-1C illustrates perspective views of a biosensor inserter 100 in accordance with one or more embodiments provided herein. Biosensor inserter 100 includes a push member 102, which in the depicted embodiment, is shown as including two coupled pieces, namely a top portion 102T and a bottom portion 102B that are coupled together. Biosensor inserter 100 further includes a contact member 106 that is translatable axially (along axial axis 105) relative to the push member 102 in the direction shown by arrow 107. Thus, contact member 106 can be received axially within the push member 102 and may be telescopic therewith. Push member 102 is the portion contacted and pushed upon by the user during biosensor insertion. Push member 102 may optionally be constructed as one piece.

Figure 1D:
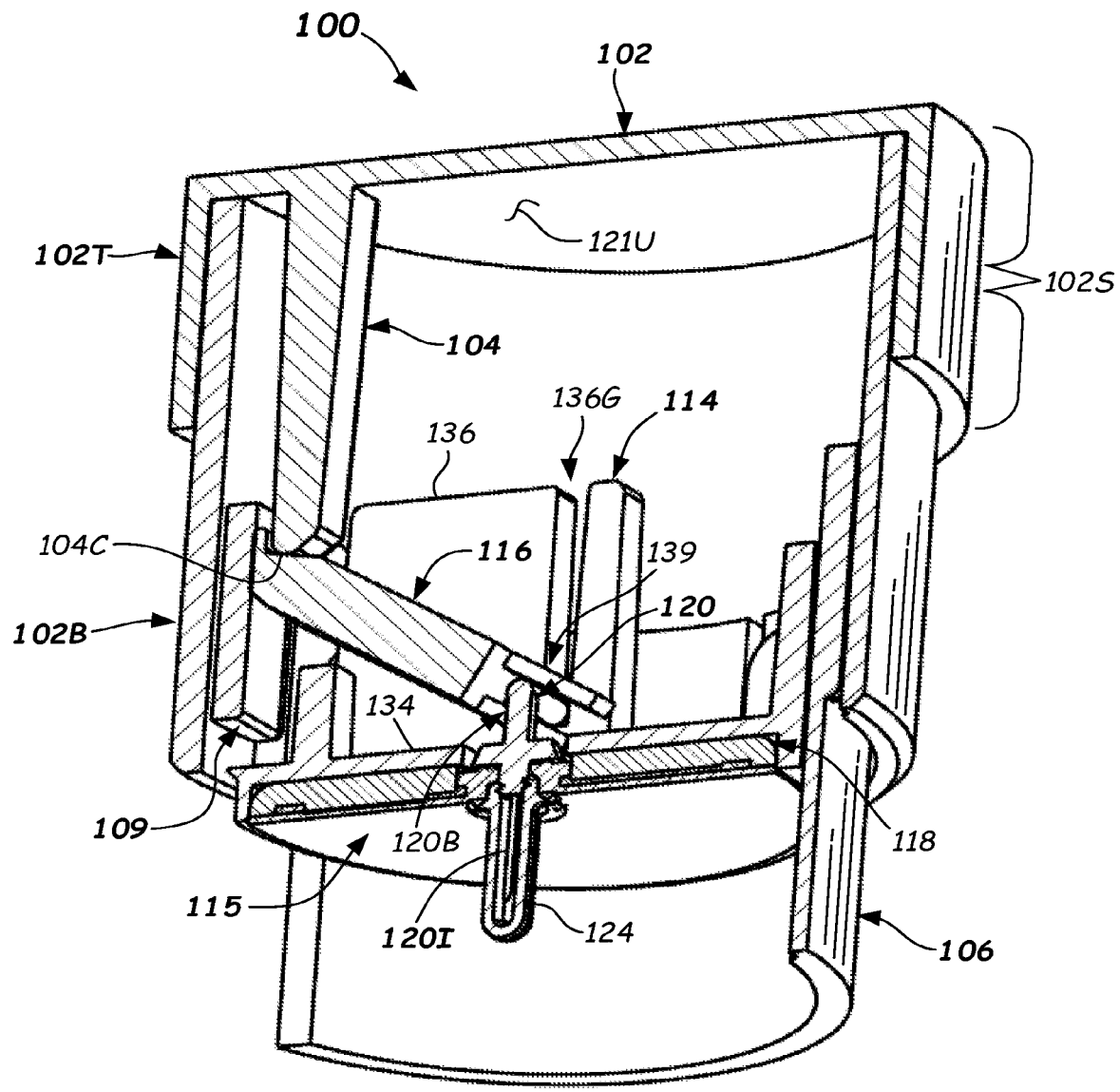
FIG. 1D is a cross-sectioned side perspective view of a biosensor inserter illustrating the various components and their interconnections in accordance with one or more embodiments provided herein.
Figure 1E:
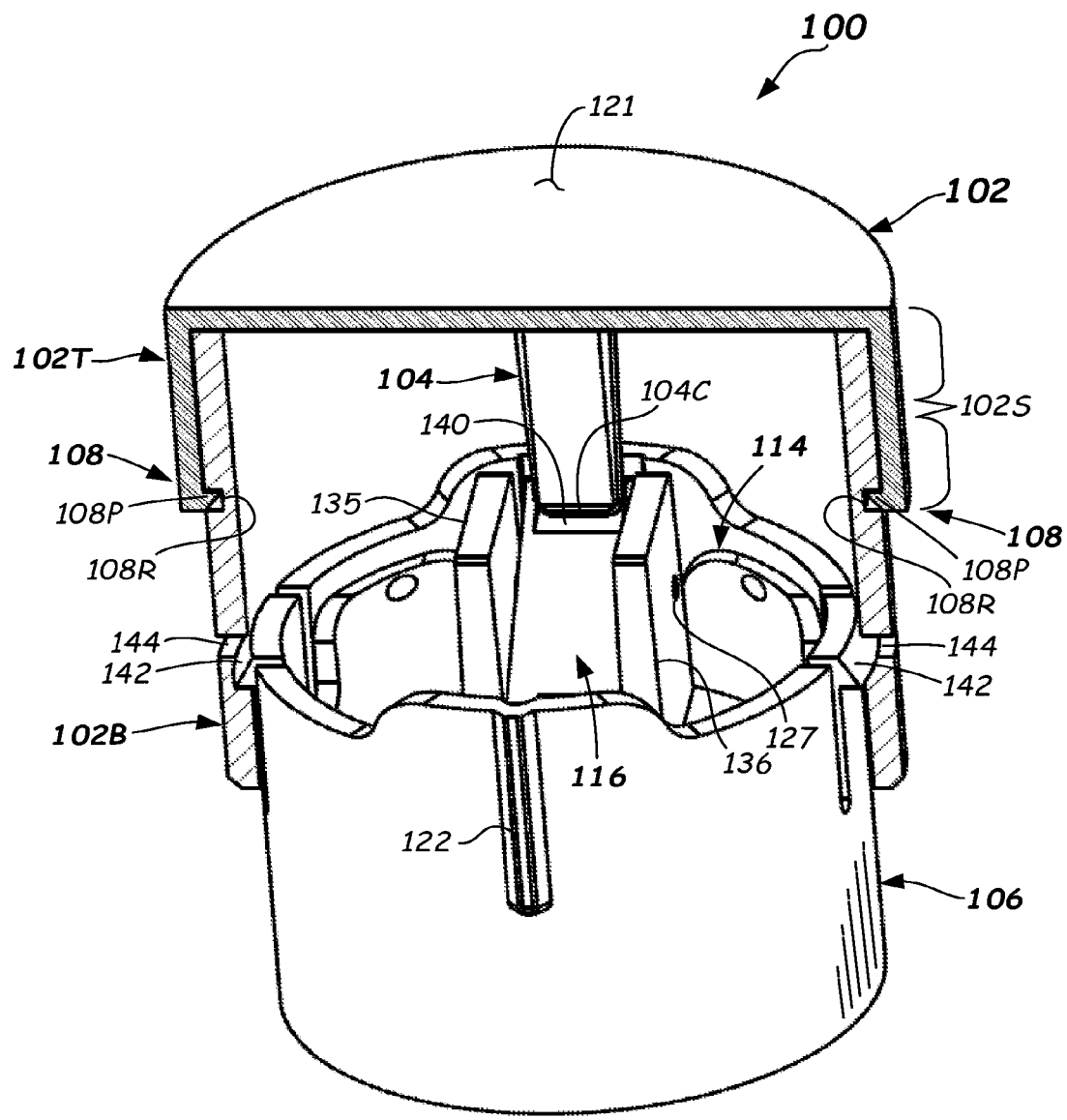
FIG. 1E is a partially cross-sectioned side perspective view of a biosensor inserter illustrating the various components and a perspective view of the assembly of contact member and transmitter carrier in accordance with one or more embodiments provided herein.
Figure 1F:
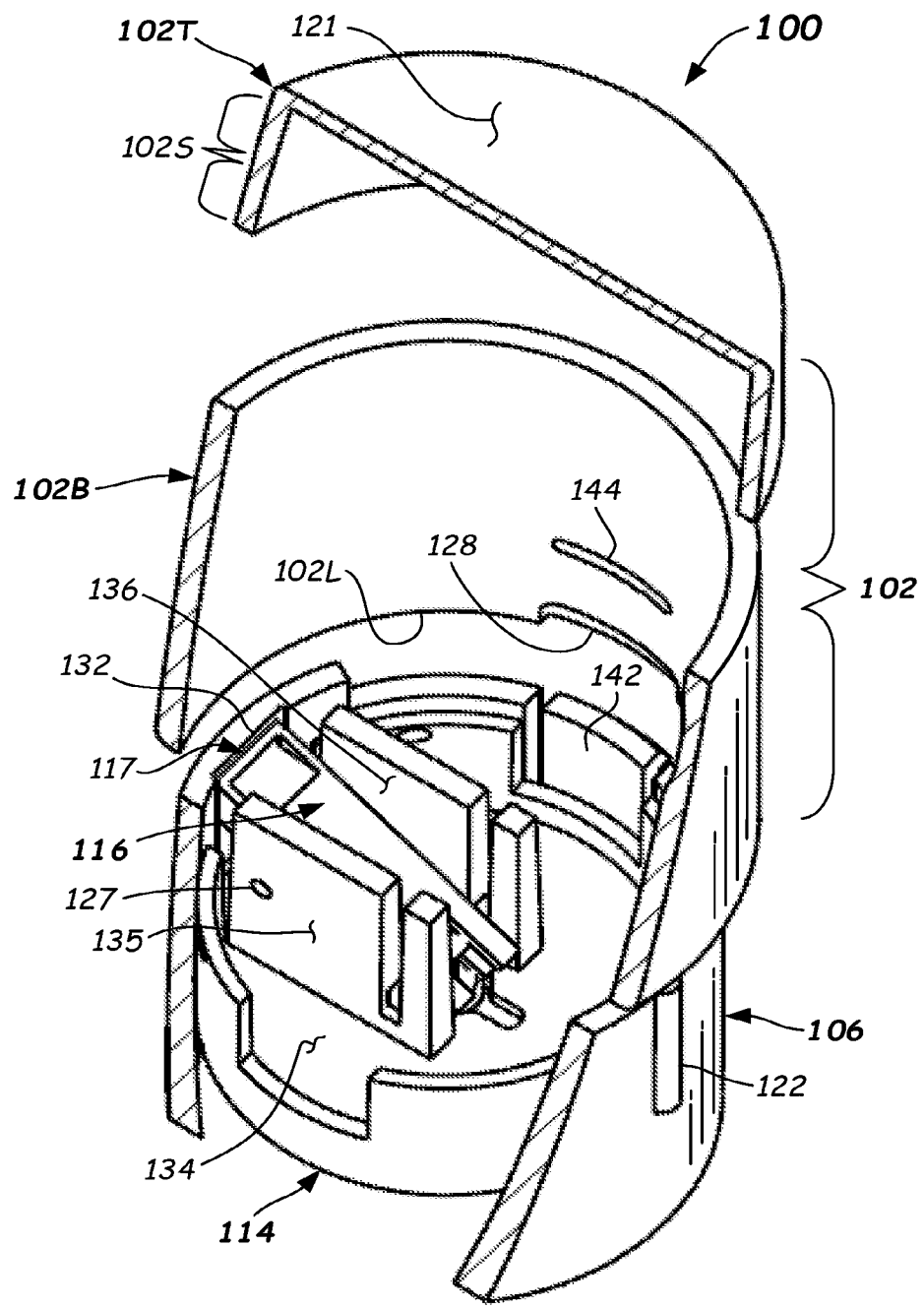
FIG. 1F is a partially exploded, partial perspective view of a biosensor inserter illustrating another view of the various components in accordance with one or more embodiments provided herein.
Figure 1G:
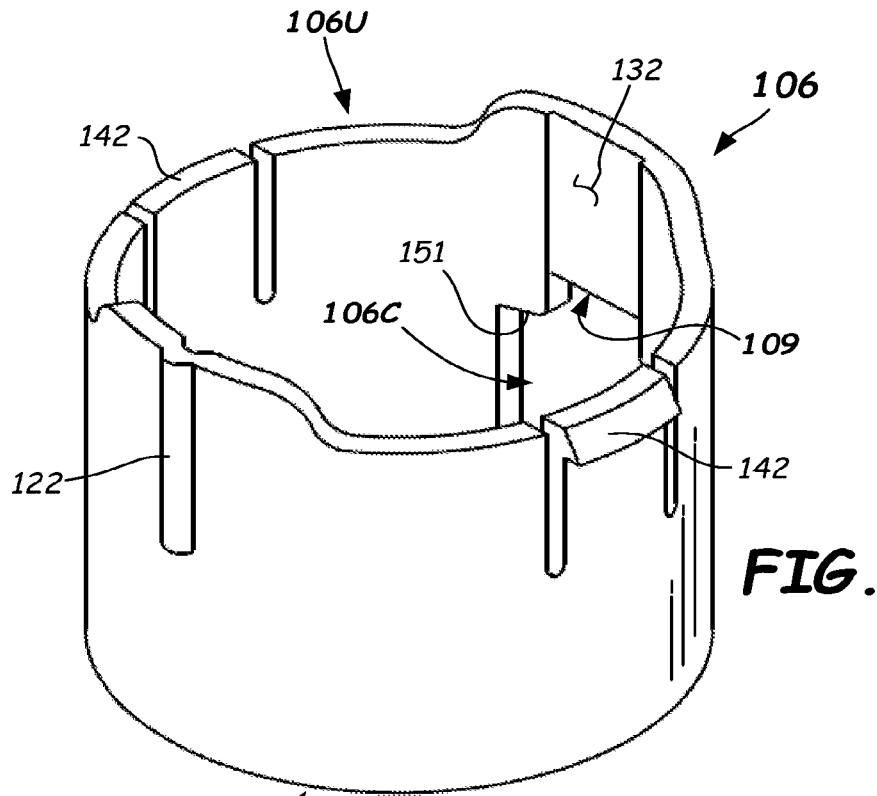
FIG. 1G is a first side perspective view of a contact member of a biosensor inserter in accordance with one or more embodiments provided herein.
Figure 1H:
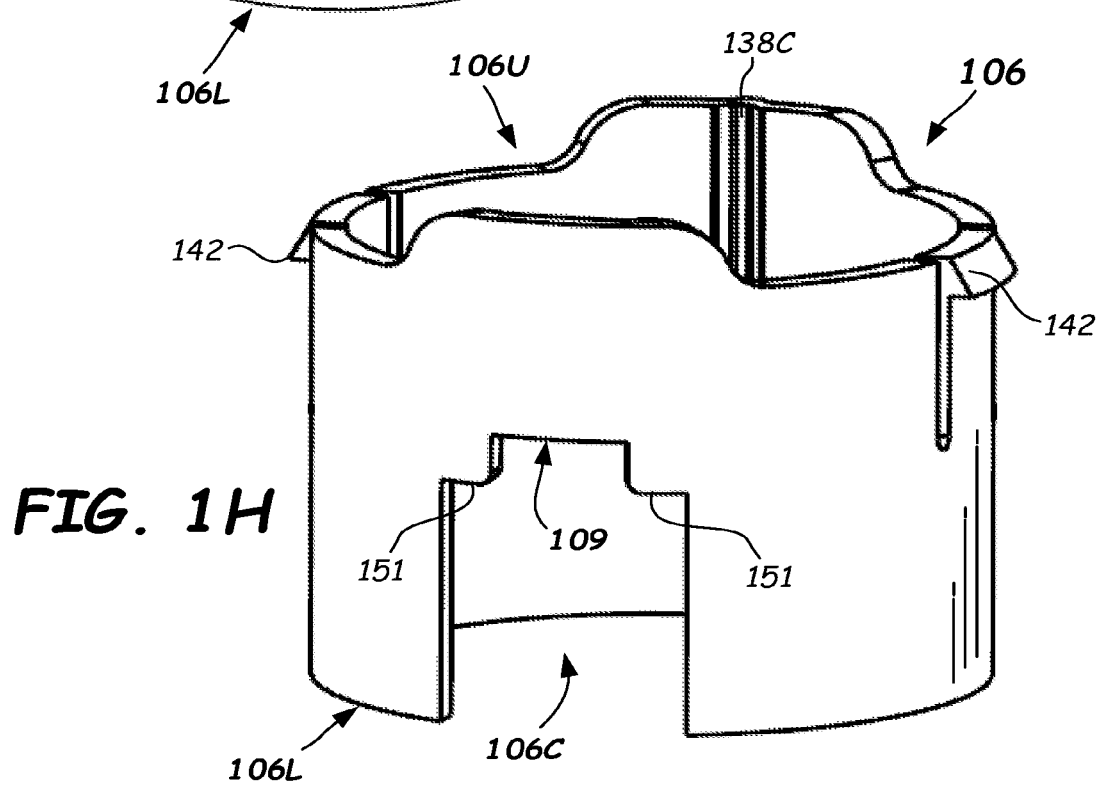
FIG. 1H is a second side perspective view of an opposite side of the contact member of FIG. 1G in accordance with one or more embodiments provided herein.
Figure 1I:
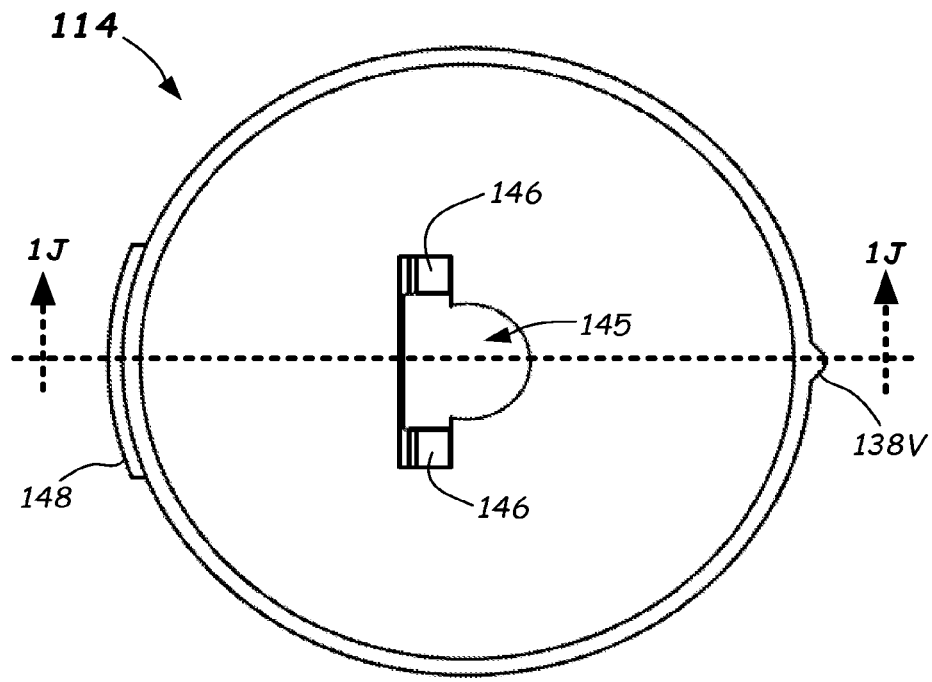
FIG. 1I is a bottom plan view of a transmitter carrier of a biosensor inserter in accordance with one or more embodiments provided herein.

As best shown in FIGS. 1G and 1H, the contact member 106 includes an upper end 106U and a lower end 106L. Lower end 106L may contact a user's skin 113 (FIGS. 2A-2F) during insertion and retraction of an insertion device 120 to implant a biosensor 150 (See FIGS. 2B and 2C) therein. Contact member 106 further includes a latch 109 (FIG. 1D), which is a latch surface (lower latch surface) that once passed by via motion of a latch end 117 (FIGS. 1L-1M) of the pivot member 116 (FIGS. 1N-1P) will allow a pivot member 116 to rotate (FIGS. 2D-2F), as will be described further herein. Up until when the latch end 117 passes by the latch 109, the pivot member 116 is restrained from rotation. The latch 109 (FIG. 1D) of the contact member 106 can be formed as part of a vertically-extending cutout 106C (FIGS. 1A-1C), and latch 109 can comprise a circumferentially-disposed surface of a width wider than the latch end 117 of the pivot member 116. Vertically-extending cutout 106C may be open at the lower end 106L.

As shown in FIGS. 1A-1F, the push member 102 can include a top member 102T and a bottom member 102B, wherein the bottom member 102B is coupled to the top member 102T as shown. Bottom member 102B can comprise a sleeve shape and the top member 102T can comprise an inverted cup that may be receivable over the sleeve. In more detail, the inverted cup comprises a top portion 121 (FIG. 1D), which can comprise a circular planar surface, and an annular sleeve portion 102S. A push element 104 (FIG. 1D-1E) extends downwardly from the push member 102 and includes a contact end 104C. The push element 104 is a rigid member and extends downwardly (as oriented) from the underside 121U of the top portion 121 and is provided in contact with the pivot member 116.

As best shown in FIGS. 1A-1C and 1E, top member 102T and bottom member 102B may be coupled together by any suitable means, such as by having two or more spring tabs 108 each including an inward protuberance 108P (FIG. 1E) being seated in a retaining feature 108R, such as a slot or groove formed in the bottom portion 102B. The inward protuberances 108P functionally snap into and lock into the respective retaining features 108R of the bottom member 102B to retain the two together as one piece. Optionally, however, the push member 102 could be molded as one piece in some embodiments. Furthermore, other means for allowing a snap-fit connection of the top member 102T to the bottom member 102B or otherwise coupling top member 102T and bottom member 102B may be used. In some embodiments, as shown in FIG. 1F, push member 102 can comprise a ramp 128 proximate a lower end 102L thereof, and the contact member 106 can include an inward protuberance 142 such as a snap fitting hook configured to engage with the ramp 128 upon assembly. If multiple inward protuberances 108P are used, there may be a corresponding ramp 128 for each.

In some embodiments, the push member 102 and/or contact member 106 may be formed from a biodegradable and/or recyclable material (e.g., a recyclable plastic, a biodegradable paper product, bamboo, etc.). In other embodiments, push member 102 and/or contact member 106 may be formed from one or more polymer materials such as, but not limited to, acrylonitrile butadiene styrene (ABS), polycarbonate, nylon, acetal, polyphthalamide (PPA), polysulfone, polyethersulfone, polyetheretherketone (peek), polypropylene, high-density polyethylene (HDPE), and low-density polyethelene (LDPE). Other suitable materials may be used for the push member 102 and/or contact member 106.

FIG. 1B illustrates a perspective underside view of the example biosensor inserter 100 in accordance with one or more embodiments provided herein. With reference to FIG. 1B, biosensor inserter 100 may include a transmitter and sensor assembly 115 detachably mounted to a transmitter carrier 114 (see also FIGS. 1C and 1D), such as in recess 118 (FIG. 1D). The transmitter carrier 114 is axially translatable relative to the contact member 106 and configured to support the transmitter and sensor assembly 115 during insertion of a biosensor 150 (FIGS. 1U, 1V, and 2A-2D). In particular, the transmitter and sensor assembly 115 may include transmitter electronics, a power source, and a sensor assembly that includes biosensor 150. Thus, the transmitter and sensor assembly 115 is supported during insertion of the biosensor 150.

In some embodiments, the transmitter and sensor assembly 115 may include a base that supports transmitter electronics, a power source (e.g., one or more batteries), and a sensor assembly (e.g., a biosensor such as an analyte sensor for determining the concentration of one or more analytes). Example transmitter electronics may include an analog front end for biasing an analyte sensor and for sensing current that passes through the biosensor 150, such as operational amplifiers, current sensing circuitry, etc. Other transmitter circuitry may include processing circuitry such as analog-to-digital converters for digitizing current signals, memory for storing digitized current signals, a controller such as a microprocessor, microcontroller or the like for possibly computing analyte concentration values based on measured current signals, and transmitter circuitry for transmitting analyte concentration values to an external device (e.g., a smart phone or another suitable external device for storing and/or displaying analyte concentrations). In some embodiments, the transmitter electronics may form a separate transmitter unit, which may be reusable and that couples with a sensor unit of a base unit having the power source and sensor assembly. The base unit may be disposable. In such embodiments, the transmitter electronics may be attached to the base unit before or after the biosensor 150 is inserted using the biosensor inserter 100.

In some embodiments, the sensor (e.g., biosensor 150) used within the transmitter and sensor assembly 115 may include two electrodes and the bias voltage may be applied across the pair of electrodes. In such cases, current may be measured through the sensor. In other embodiments, the sensor may include three electrodes such as a working electrode, a counter electrode, and a reference electrode. In such cases, the bias voltage may be applied between the working electrode and the reference electrode, and current may be measured through the working electrode, for example. The sensor may include an active region including one or more chemicals that undergo an analyte-enzyme reaction with the products they detect. The enzyme is immobilized on one or more electrodes to provide a reaction (e.g., redox reaction) with the analyte and generate a current at the electrodes. For example, the reaction may affect the concentration of charge carriers and the time-dependent impedance of the sensor. Example chemicals include glucose oxidase, glucose dehydrogenase, or the like. In some embodiments, a mediator such as ferricyanide or ferrocene may be employed at the active region. In one or more embodiments, a sensor may include a microneedle or a plurality of microneedles, such as a microneedle array. In general, analytes that may be detected and/or monitored with a suitable sensor include glucose, cholesterol, lactate, uric acid, alcohol, or the like. An analyte is defined herein as a component, substance, chemical species, or chemical constituent that is measurable in an analytical procedure.

An example biosensor 150 (FIG. 1U) can be any suitable implantable sensor that can be implanted in the skin 113 (FIG. 2A) of a user, such as a strand-shaped sensor that is able to be received inside of the insertion portion 120I of the insertion device 120 and that is able to sense an analyte concentration reading of an interstitial fluid under the skin 113, such as a glucose sensor, lactate sensor, or the like.

Figure 1J:
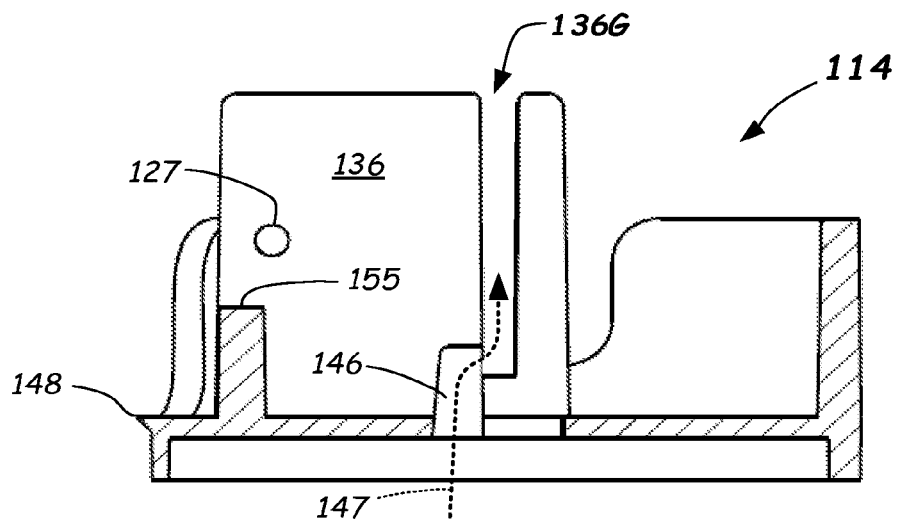
FIG. 1J is a cross-sectioned side view of a transmitter carrier of FIG. 1I taken along section line 1J-1J in accordance with one or more embodiments provided herein.
Figure 1K:
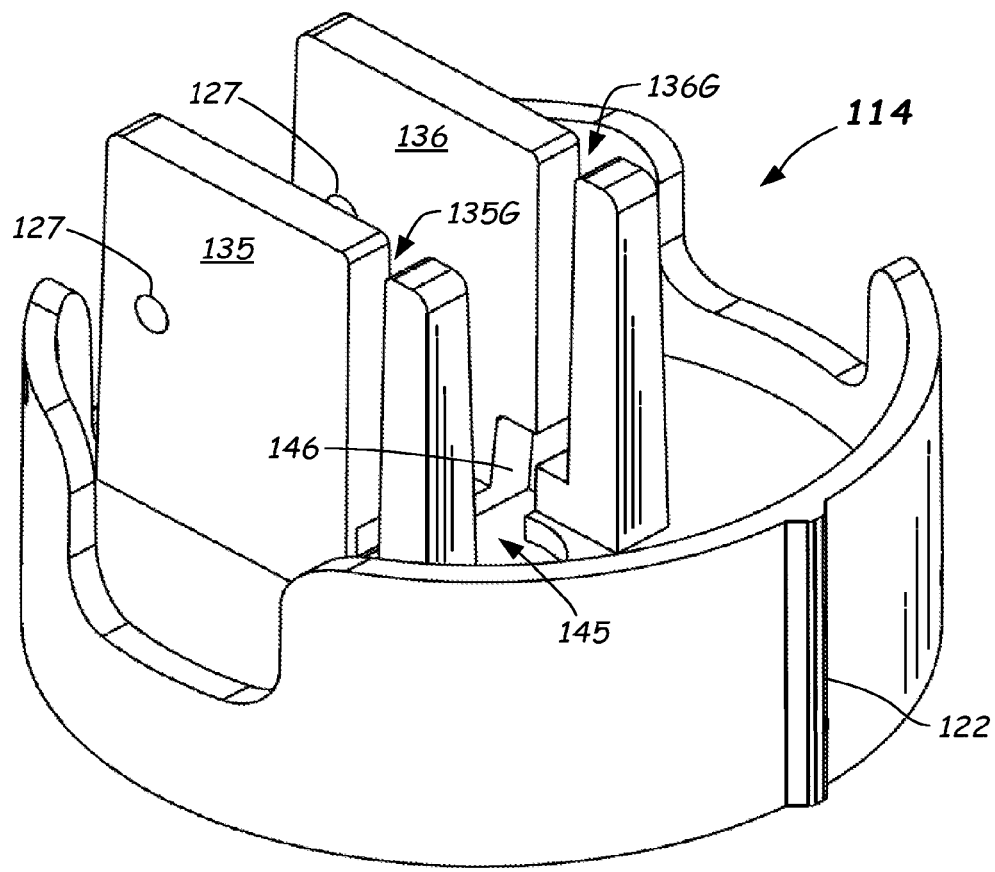
FIG. 1K is a perspective side view of a transmitter carrier of a biosensor inserter in accordance with one or more embodiments provided herein.
Figure 1L:
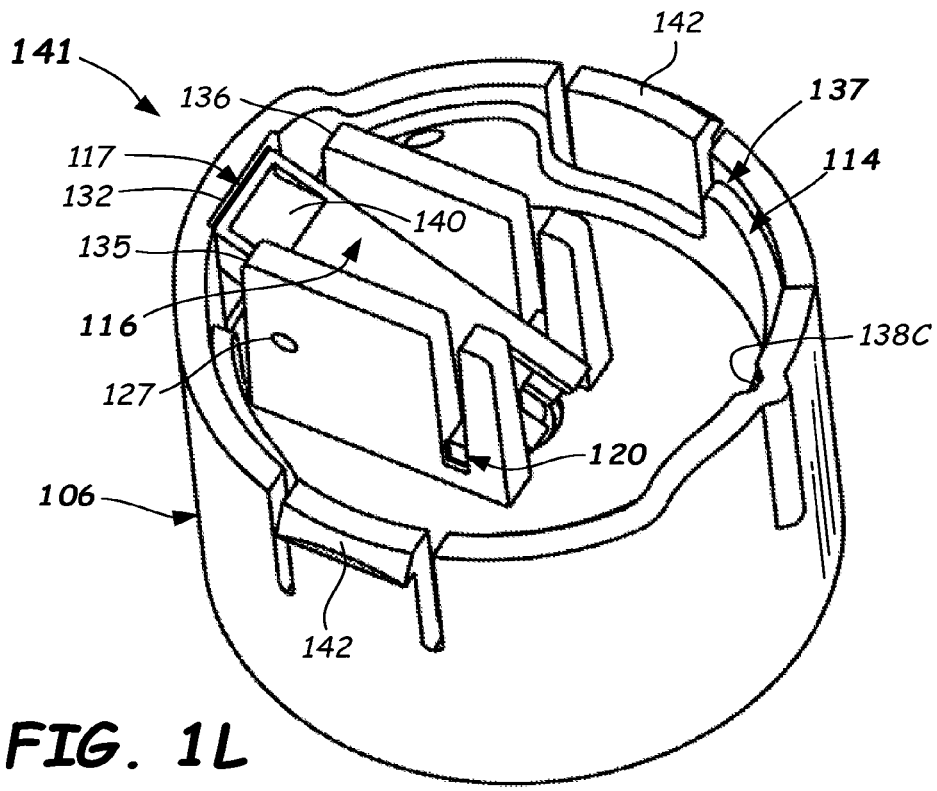
FIG. 1L is a perspective side view of an assembly of a contact member and carrier assembly of a biosensor inserter in accordance with one or more embodiments provided herein.
Figure 1M:
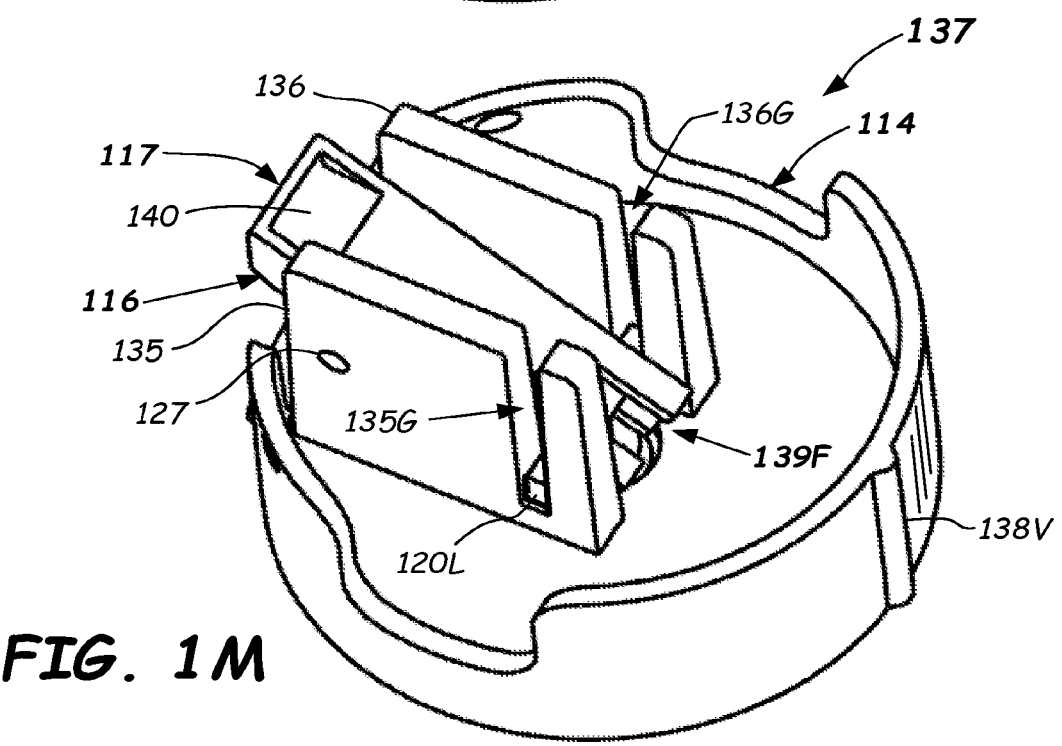
FIG. 1M is a perspective side view of a carrier assembly of a biosensor inserter in accordance with one or more embodiments provided herein.
Figure 1N:
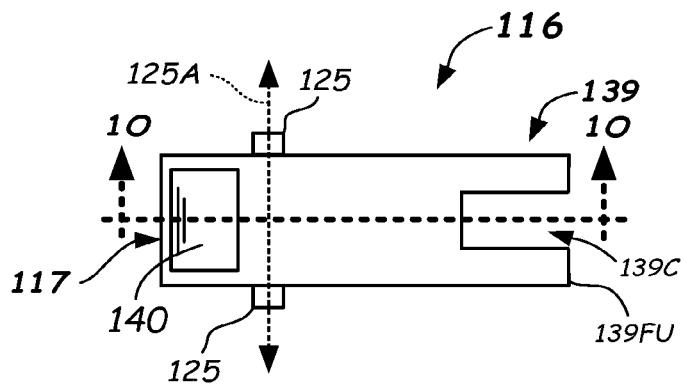
FIG. 1N is a top plan view of a pivot member of a biosensor inserter in accordance with one or more embodiments provided herein.
Figure 1O:
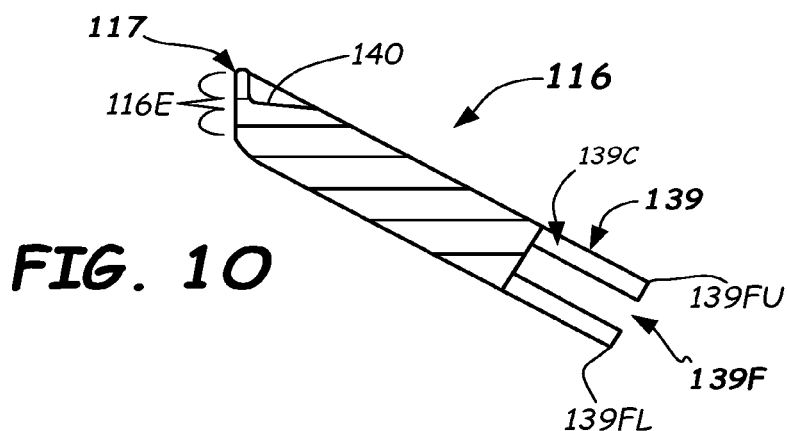
FIG. 1O is a cross-sectioned side view of a pivot member of FIG. 1N taken along section line 10-10 in accordance with one or more embodiments provided herein.
Figure 1P:
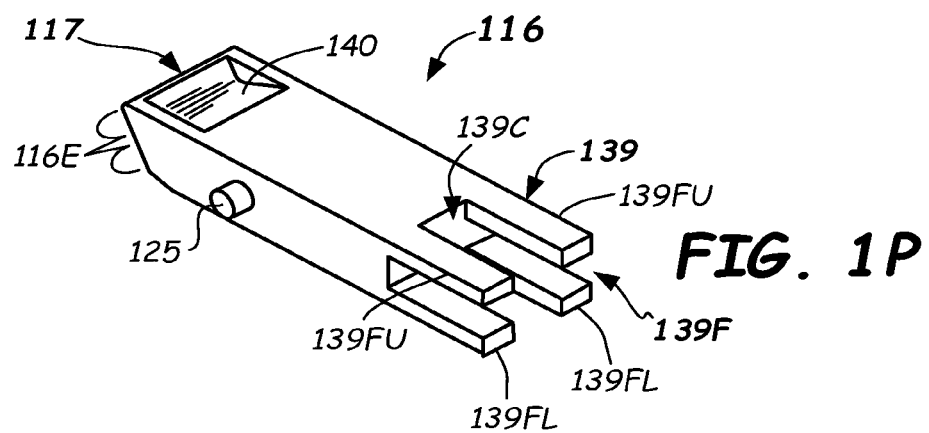
FIG. 1P is a perspective view of a pivot member in accordance with one or more embodiments provided herein.
Figure 1Q:
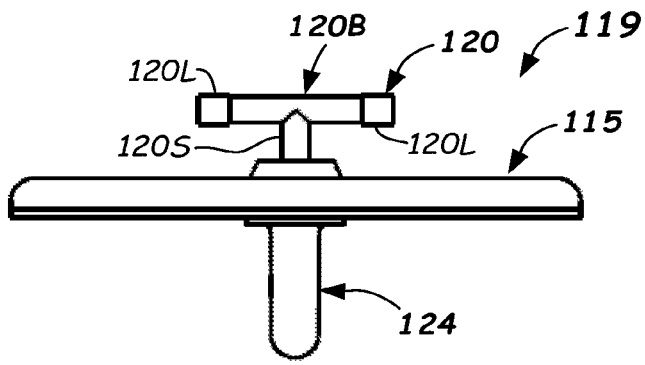
FIG. 1Q is a side plan view of a transmitter-insertion assembly including a transmitter and sensor assembly with a coupled insertion device in accordance with one or more embodiments provided herein.
Figure 1R:
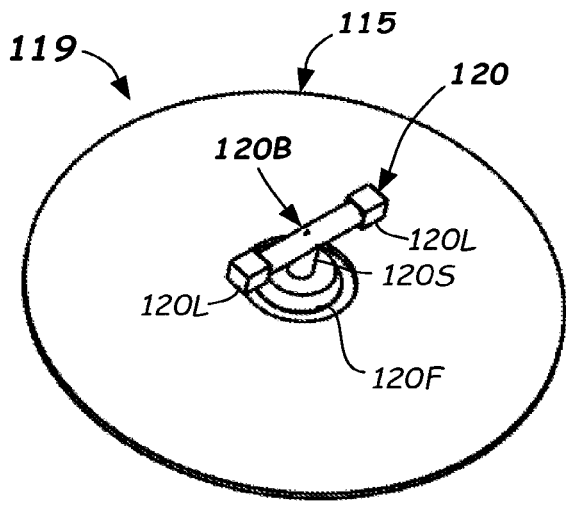
FIG. 1R is a perspective view of a transmitter-insertion assembly in accordance with one or more embodiments provided herein.
Figure 1S:
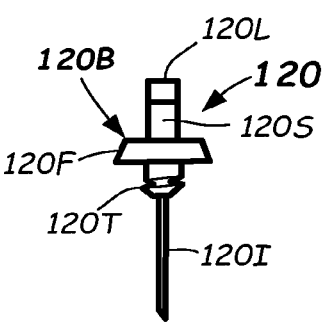
FIG. 1S is a first side plan view of an insertion device in accordance with one or more embodiments provided herein.
Figure 1T:
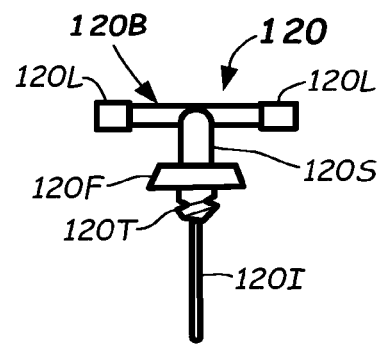
FIG. 1T is a second side plan view of an insertion device in accordance with one or more embodiments provided herein.

As shown in FIGS. 1Q and 1R, in some embodiments, a transmitter-insertion assembly 119 that is an assembly of the insertion device 120 (shown in FIG. 1S through 1V) and the transmitter and sensor assembly 115 is provided. The transmitter-insertion assembly 119 can include a needle cover 124, which can be removed by the user prior to carrying out the insertion method. The needle cover 124 is detachable from the insertion device 120 and shields the insertion portion 120I (e.g., needle portion) of the insertion device 120. Thus, the needle cover 124 is detachable from threads or other snap-fit features 120T formed on the body 120B of the insertion device 120. Other configurations of the needle cover 124 may be used.

As described, biosensor inserter 100 further includes a pivot member 116 that is configured to pivot on and relative to the transmitter carrier 114. Pivot member 116, as best shown in FIGS. 1N through 1P, includes a latch end 117 on a first end and may include an insertion device support feature 139 on an end opposite the first end. The insertion device support feature 139 is configured to contact, support, and drive (insert and retract) the insertion device 120 during the insertion method.

In some embodiments, the insertion device support feature 139 comprises a fork 139F configured to receive legs 120L of a body 120B of the insertion device 120 (See FIGS. 1Q-1U) therein. Fork 139F can comprise a first extending slot, which may extend fully through the lateral width of the pivot member 116 and may have an open end on the end opposite from the latch end 117 of the pivot member 116, thus forming the fork 139F. Upper prong 139FU and lower prong 139FL of the fork 139F may be configured to receive legs 120L of a body 120B there between. A stem 120S (FIGS. 1S-1U) of the body 120B, from which the legs 120L laterally extend, may be received in and through a vertical clearance 139C (FIGS. 1N-1P). A second extending slot can extend vertically through at least the lower fork member 139FL to intersect with the laterally-extending slot and form the vertical clearance 139C. The slots can be sized to receive the legs 120L and stem 120S of the body portion 120B of the insertion device 120. Upper and lower as used herein refer to the orientation shown in FIG. 2B, but it should be recognized that the pivot member 116 and other elements may be oriented in other orientations when in use.

Pivot member 116 may also include one or more pivot features that allow the pivot member 116 to pivot relative to the transmitter carrier 114. For example, pivot member 116 may include laterally-extending features 125 (e.g., posts) that interface with holes 127 in first and second side supports 135 and 136 of transmitter carrier 114 (see FIG. 1K) to form a pivot axis 125A. Thus, the pivot member 116 is pivotable about the pivot axis 125A and pivots on the transmitter carrier 114.

A pivot location of the pivot member 116 can be formed between the first end and the opposite end of pivot member 116. For example, pivot axis 125A (FIG. 1N) may be formed by laterally-extending features 125, such as cylindrical post extensions, that project from the respective lateral sides of the body of the pivot member 116. The laterally-extending features 125 can be received in the holes 127 (FIGS. 1J-1M) formed in opposite side supports 135, 136 of the transmitter carrier 114. The pivot member 116 can include a push element interface feature 140, which may comprise a pocket or other interface feature formed between the pivot axis 125A and the latch end 117 that is configured to interface with and contact a contact end 104C (FIG. 1D) of the push element 104. Other suitable laterally-extending features may be used to form the pivot. Other pivot mechanisms may be used, such as a removable axle, or the like.

In some embodiments, transmitter carrier 114 and/or pivot member 116 may be formed from a plastic material such as, but not limited to, acrylonitrile butadiene styrene (ABS), polycarbonate, nylon, acetal, polyphthalamide (PPA), polysulfone, polyethersulfone, polyetheretherketone (peek), polypropylene, high-density polyethylene (HDPE), and low-density polyethelene (LDPE). Other materials may be used for transmitter carrier 114 and/or pivot member 116.

Figure 2A:
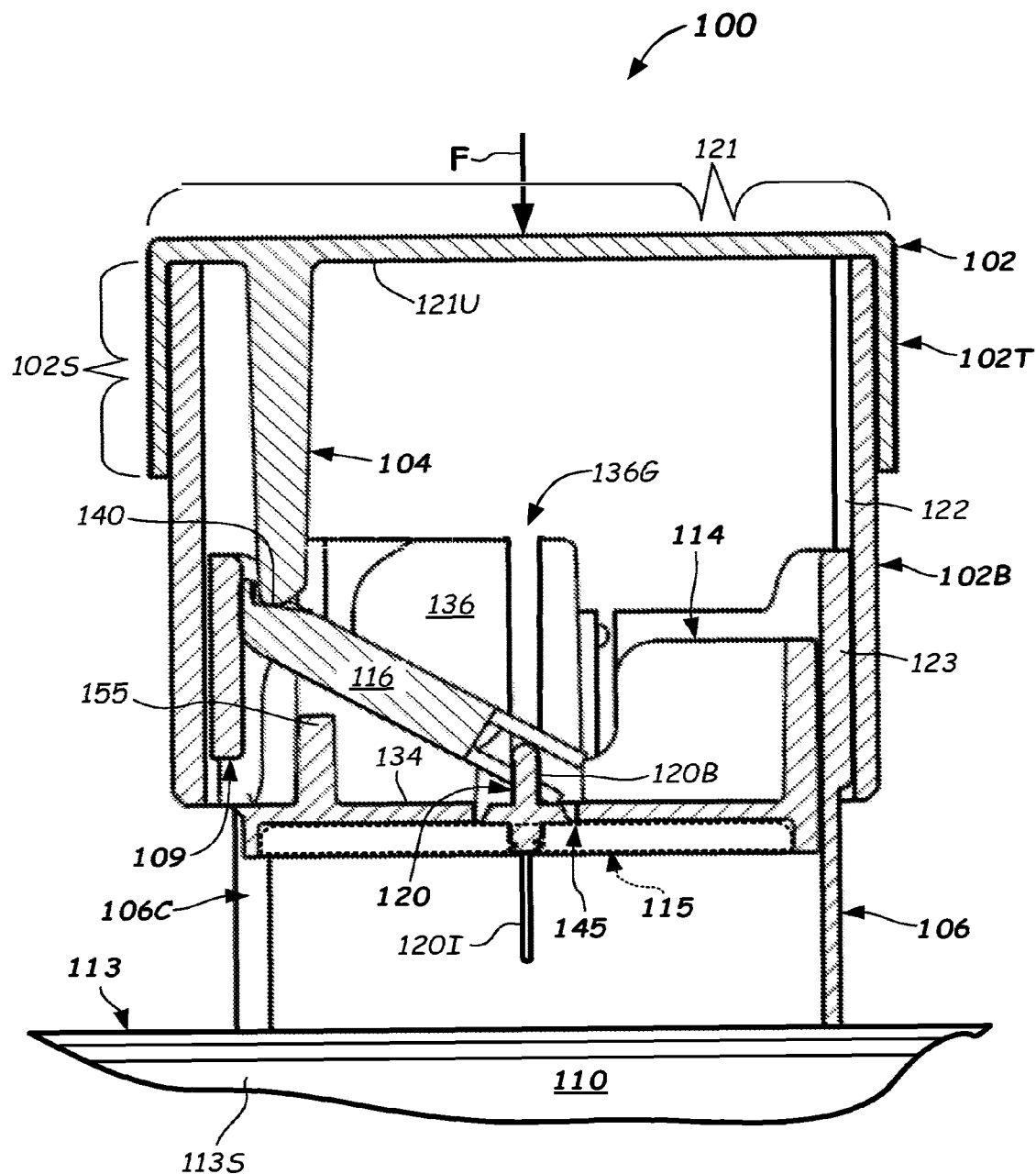
FIGS. 2A-2F illustrates multiple side cross-sectional views of a biosensor inserter during various stages of a method of insertion of a biosensor in accordance with embodiments provided herein.
Figure 2B:
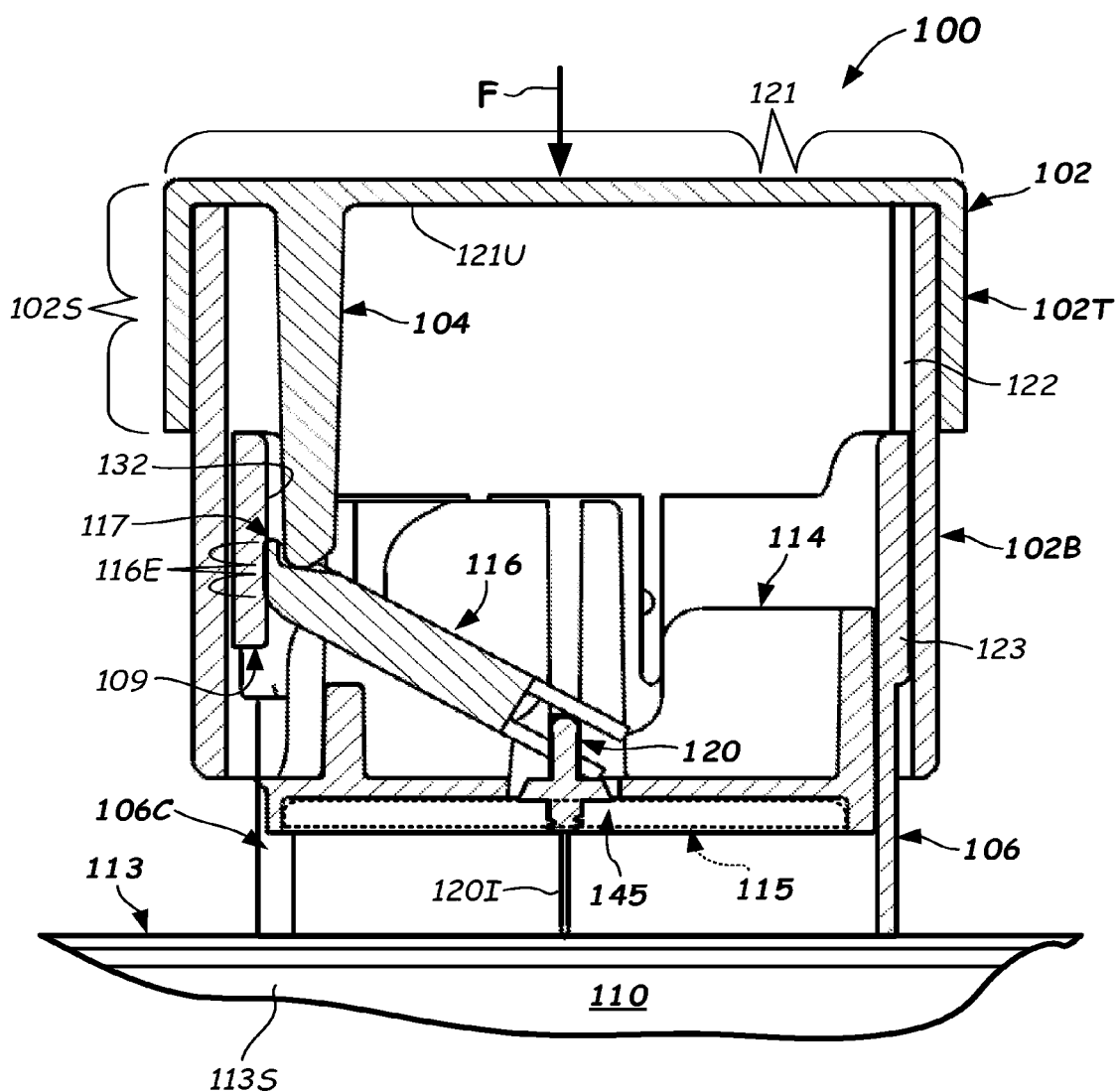
Figure 2C:
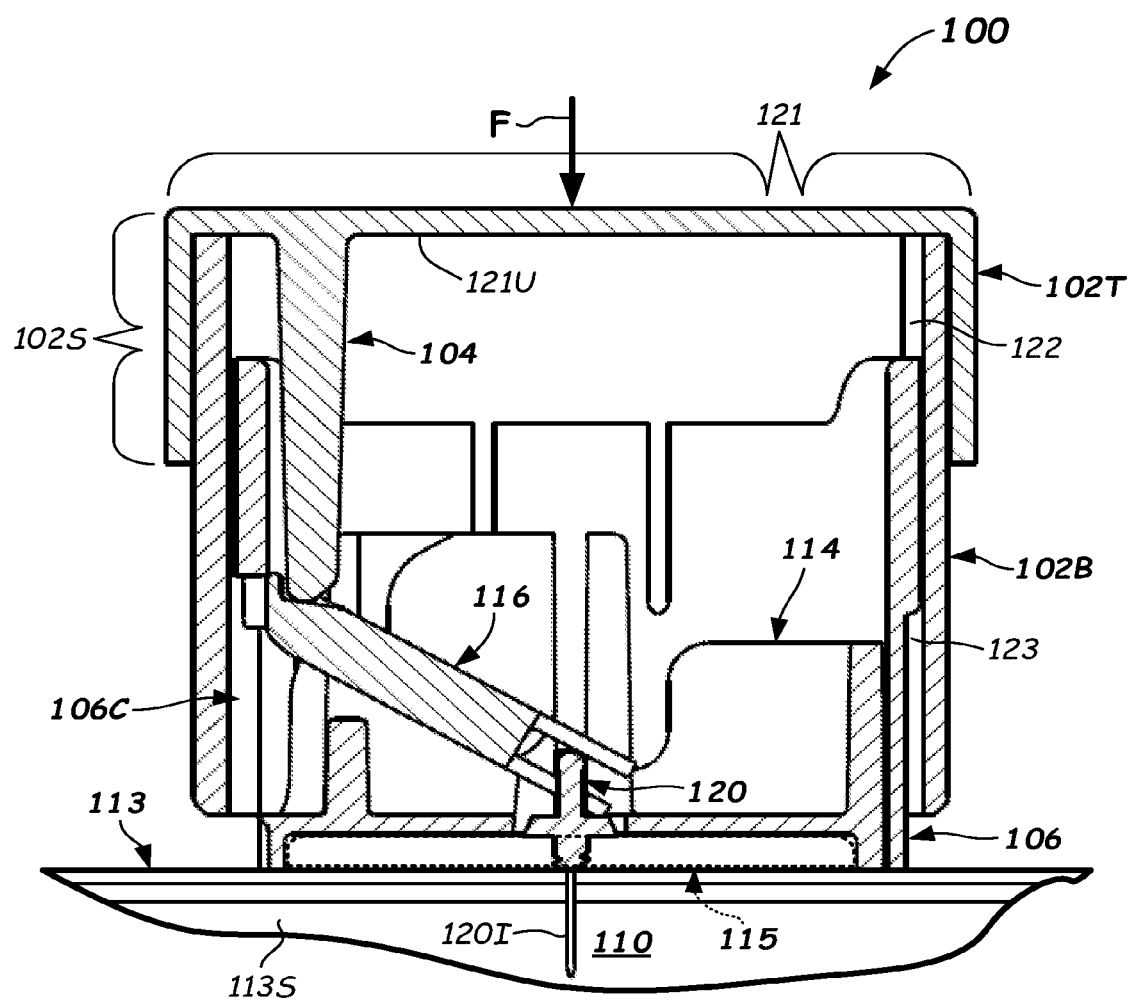

In operation, insertion device 120 is drivable by being contacted by the pivot member 116 in an insertion stroke to insert the biosensor 150 into the user's skin 113 as shown in FIGS. 2B and 2C. The insertion device 120 is drivable by the legs 120L of the body 120B being received in the fork 139F of the pivot member 116. Further, the legs 120L may each include rectangular portions at their respective outer ends that are received in guides 135G, 136G (FIG. 1M) of transmitter carrier 114, which can be vertically oriented slots, and which may be open at the top end. The fit of the rectangular portions and the guides 135G, 136G may be a slip fit, which can aid in restraining rotation of the insertion device 120 during insertion. Thus, guides 135G, 136G and rectangular ends on legs 120L may interface and provide an anti-rotation support along an axis passing laterally through the legs 120L. Transmitter carrier 114 may further include a convex alignment member 138V (FIGS. 1I, 1K, and 1M), such as a vertically-extending rib (e.g., rounded rib shown), that is configured to interface with a concave alignment member 138C of contact member 106, such as recess shown in FIG. 1L.

As best shown in FIGS. 1D and 1E, contact member 106 may be configured to be concentric with push member 102 and may be telescopic therewith. In some embodiments, push member 102 may include a first alignment feature 122 (See FIG. 1E and FIG. 2A) such as a vertically-extending groove or recess, and contact member 106 may include a second alignment feature 123 (FIG. 2A), such as a vertically extending rib, that interfaces with the first alignment feature 122. Such alignment features 122, 123 may hold push member 102 and contact member 106 in rotational alignment to prevent rotation of the contact member 106 within the push member 102, such as during the insertion and retraction portions of the stroke. Push member 102 and contact member 106 may be cylindrical, oval, oblong, elliptical, or any other suitable shape in transverse cross-section. In some embodiments, push member 102 and contact member 106 may not be concentric.

In more detail, transmitter carrier 114 shown in FIG. 1I-1M is configured to support the transmitter and sensor assembly 115 during insertion of the biosensor 150 of the transmitter and sensor assembly 115. Transmitter carrier 114 may be sized to fit within contact member 106 as shown in FIG. 1L, which shows an assembly 141 of contact member 106, transmitter carrier 114, pivot member 116, and insertion device 120.

As best shown in FIG. 1A-1E, in some embodiments, contact member 106 may include a first pre-insertion lock feature 142 configured to retain the contact member 106 relative to the push member 102 until a certain pre-designed axial force is exceeded. After the pre-designed force is exceeded, the contact member 106 may move further axially into the push member 102. For example, first pre-insertion lock feature 142 can be configured to extend into a second pre-insertion lock feature 144, such as a window shown or groove formed in push member 102 so as to prevent push member 102 from sliding over contact member 106 prior to insertion, as described below with reference to FIGS. 2A-2F. However, after the pre-designed force is overcome through application of an axial force F by the user on the push member 102, the first pre-insertion lock feature 142 can flex and move axially inside and along the inner surface of the push member 102 so that relative axial sliding motion of the contact member 106 into the push member 102 is allowed. First pre-insertion lock feature 142 may be a spring tab including a hook or the like seated in the groove or slot as shown in FIG. 1E. Once the pre-designed force is overcome, the axial force F may vary slightly over the remainder of the stroke.

FIG. 1F is an exploded, partial cross-sectioned, side-perspective view of the example biosensor inserter 100 with a portion of outer member 102 and inner member 106 removed for illustrative purposes, in accordance with embodiments provided herein. FIGS. 1F and 1G illustrate an internal guide feature 132 formed on an inside surface of contact member 106 along which an end (e.g., planar end 116E—FIG. 1O) of the pivot member 116 may axially slide during at least part of the stroke of the insertion method, as described further herein. The guide feature 132 may be a planar-bottomed groove slightly wider than a width of the pivot member 116. The guide feature 132 may intersect with the latch 109 (FIG. 1G), at its lower end. Internal guide feature 132 may be axially-disposed and receive the end 116E of the pivot member 116 and restrain rotation of the pivot member 116 over the first portion of the stroke, wherein rather than rotate, the end 116E slides vertically along the guide feature 132 and is restrained from rotation. Note that other types of the internal guide feature 132 may be used. For example, inner member 106 may have a protruding alignment feature such as a rib received in a groove formed in the end of the pivot member 116 for guiding pivot member 116.

With further reference to FIG. 1D, transmitter carrier 114 may be formed from a cylindrical body that includes a base 134, which is used to support the transmitter and sensor assembly 115 during insertion (as described further herein) The base 134 also couples to supporting structure, which is configured to support the pivot member 116. As best shown in FIGS. 1J-1K, supporting structure may include the first support 135 having a first guide 135G and a second support 136 having a second guide 136G. Guides 135G and 136G may comprise slots that can be axially oriented and extending and may be employed to guide the insertion device 120 (FIGS. 1S-1U) during the insertion method, as described further herein. Insertion device 120 slides into insertion device support feature 139 of pivot member 116 (e.g., into the fork 139F), and also into guides 135G and 136G of first and second side supports 135 and 136 straddling the pivot member 116.

As best shown in FIG. 1D, push element 104 may extend downward from the underside 121U of the top portion 121 and may include a contact end 104C. Push element 104 may be substantially rigid and may extend generally perpendicularly from the underside 121U, and may be offset, as shown, from the axial axis 105. Push element 104 may include a contact end 104C that contacts, and pushes on, the pivot member 116 during the insertion method. In some embodiments, contact end 104C may include a cylindrical end portion that contacts the push element interface feature 140 (e.g., a pocket as shown in FIG. 1L, for example). During insertion, the push element 104 does not bend or deform in any substantial way, so that pushing on the push member 102 telescopes the contact member 106 within the push member 102 and linearly translates both the pivot member 116 and the transmitter carrier 114 towards the user's skin 113 during the insertion portion of the stroke.

Example dimensions of push element 104 range from about 25 mm to 35 mm long, 5 mm to 15 mm wide, and 3 mm to 10 mm thick. Other dimensions may be used. Example materials for push element 104 and pivot member 116 include acrylonitrile butadiene styrene (ABS), polycarbonate, nylon, acetal, polyphthalamide (PPA), polysulfone, polyethersulfone, polyetheretherketone (peek), polypropylene, high-density polyethylene (HDPE), and low-density polyethelene (LDPE). Other materials may be used.

Assembly and operation (the insertion method) of the biosensor inserter 100 is now described with reference to FIGS. 2A-2F, which illustrate side cross-sectional views of the biosensor inserter 100 during the insertion method of a biosensor 150 in accordance with embodiments provided herein.

To assemble the biosensor inserter 100, the transmitter-insertion assembly 119 made up of the transmitter and sensor assembly 115 (FIGS. 1Q-1R) with insertion device 120 (FIGS. 1S-1V) is inserted from the bottom so that body 120B of the insertion device 120 passes through aperture 145 (FIG. 1I), up through slot ends 146, and into guides 135G, 136G in the transmitter carrier 114, along a path shown by dotted arrow 146 in FIG. 1J. Thus, the ends of legs 120L are received in the slot ends 146 and transition up and to the right in FIG. 1J into enter the guides 135G, 136G. Once the transmitter-insertion assembly 119 of transmitter and sensor assembly 115 and insertion device 120 is properly positioned in the guides 135G, 136G, it may be held in place in the transmitter carrier 114 with any suitable quick release feature, such as a slight interference fit within the recess 118 (see FIG. 1D), or possibly a small amount of double sided adhesive tape or suitable low-strength adhesive.

Next, the fork 139F (FIG. 1M) of the insertion device support feature 139 of the pivot member 116 is received over the legs 120L and the laterally-extending features 125 of the pivot member 116 are snapped into the holes 127 in the side supports 135, 136 to form the pivot aligned with pivot axis 125A.

Next, the carrier assembly 137 (FIG. 1M) made up of transmitter carrier 114 with the pivot member 116, insertion member 120, and the transmitter and sensor assembly 115 are inserted into contact member 106 as shown in FIG. 1L to form subassembly 141. The carrier assembly 137 can be inserted into the bottom of the contact member 106 until the first stop feature 148 (FIGS. 1I-1J) of the transmitter carrier 114 contacts one or more second stop features 151 formed at the end of the cutout portion 106C of the contact member 106 (See FIGS. 1G and 1H). Other suitable stop features may be used to limit the extent that the carrier assembly 137 can be inserted into the contact member 106. A slight interference fit may be provided between the outside surface of the carrier assembly 137 and the inside surface of the contact member 106 to retain the assembly 137 inside of the contact member 106.

Next, some or all of push member 102 can be installed over the subassembly 141 (FIG. 1L) as shown in FIG. 1D. The push member 102 can be installed by first installing the bottom portion 102B over the subassembly 141 until the first pre-insertion lock feature 142 snaps into the second pre-insertion feature 144. First pre-insertion lock feature 142 can be a snap-fit hook and the second pre-insertion feature 144 can be a slot or groove, for example.

Next, the top portion 102T can be installed over the over the bottom portion 102B. Upon proper alignment, the two or more spring tabs 108 each including an inward protuberance 108P can be seated in the respective retaining features 108R. Upon installation, the push element 104 is aligned with, and in close proximity to or just touching, the push element interface feature 140 of the pivot member 116. As shown, contact member 106 is sized to fit within push member 102, and may have a close sliding fit or even a slight interference fit, for example.

Now referring to FIGS. 1D, 1I, 1J, and 1U, insertion device 120 has a main body portion 120B that resides within insertion device support feature 139 (e.g., fork 139F) of pivot member 116, and an insertion portion 1201 that is extendable from the transmitter carrier 114 through an aperture 145 (FIG. 1I) in the base 134 of transmitter carrier 114. Insertion portion 1201 of insertion device 120 can have a sharpened end (FIG. 1U) that pierces the user's skin 113 (FIGS. 2A-2F) to introduce a biosensor 150 into a subcutaneous region 113S of a user as described further herein. Insertion portion 1201 also may be referred to as an insertion shaft, needle, trocar, sharp or the like. Upon retraction of the insertion portion 1201, the biosensor 150 received in an opening 1500 (slot, elongated cavity, or groove as shown, for example, in FIGS. 1U and 1V) formed along a length of the insertion portion 1201 remains in the subcutaneous region 113S of the user.

Figure 1U:
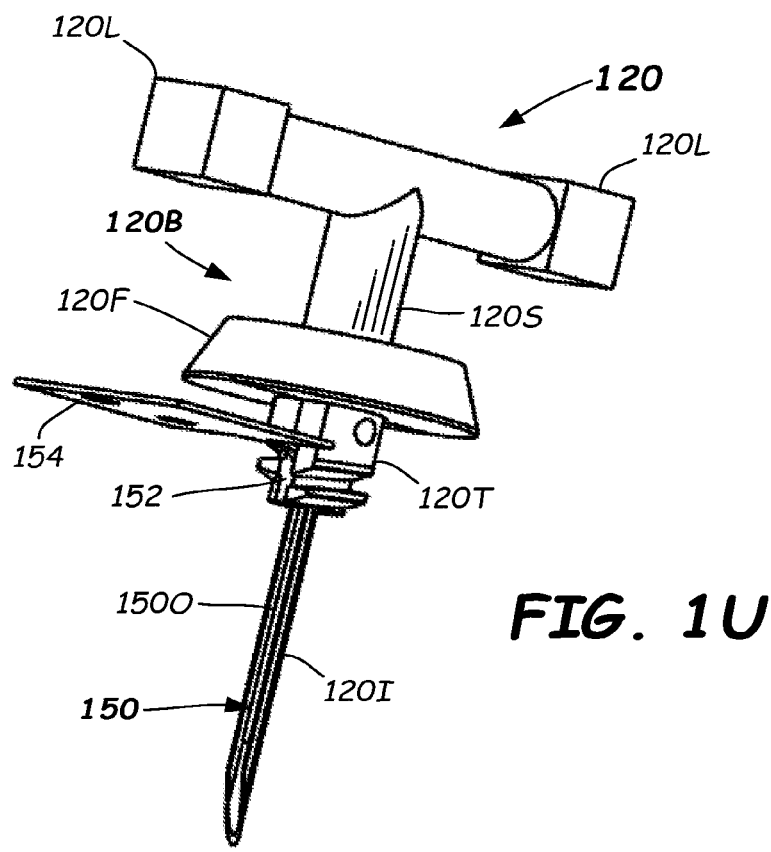
FIG. 1U is a perspective side view of an insertion device illustrating a routing of a biosensor in accordance with one or more embodiments provided herein.
Figure 1V:
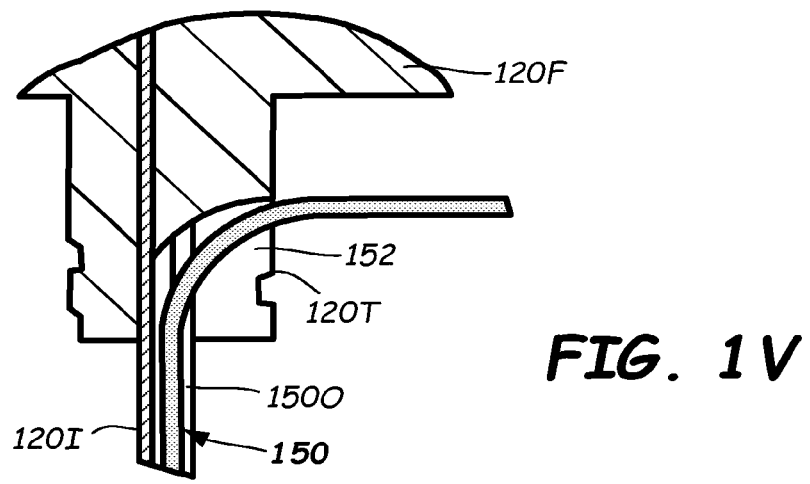
FIG. 1V is an enlarged partial cross-sectioned side view of an insertion device illustrating routing of a biosensor in accordance with one or more embodiments provided herein.

In some embodiments, aperture 145 in the base 134 of transmitter carrier 114 is positioned and/or centered below guides 135G, 136G of first and second supports 135 and 136 such that insertion portion 1201 remains approximately vertical during insertion (and/or approximately perpendicular to a region into which the insertion portion 1201 is to be inserted), as shown in FIG. 2A. Body portion 120B of the insertion device 120 may include a flange 120F (FIGS. 1S-1V) that may interface with a top surface of the transmitter and sensor assembly 115 so as to act as an alignment guide to help provide the approximately perpendicular orientation of the insertion portion 1201 to the transmitter.

Insertion portion 1201 of insertion device 120 may be made, for example, from a metal such as stainless steel, or a non-metal such as plastic. Other suitable materials may be used. In some embodiments, insertion portion 1201 of insertion device 120 may be, but is not limited to, a round C-channel tube, a round U-channel tube, a stamped sheet metal part folded into a U-profile in cross-section, a molded/cast metal part with a U-channel profile in cross-section, or a solid metal cylinder with an etched or ground channel causing a U-shapes cross-section. Other insertion portion shapes may be used that allow insertion and retraction, while leaving behind the implanted biosensor 150.

Main body portion 120B of insertion device 120 may be formed from a plastic, for example, such as, but not limited to, acrylonitrile butadiene styrene (ABS), polycarbonate, nylon, acetal, polyphthalamide (PPA), polysulfone, polyethersulfone, polyetheretherketone (peek), polypropylene, high-density polyethylene (HDPE), and low-density polyethelene (LDPE). Other materials may be used.

As best shown in FIGS. 1U and 1V, the biosensor 150 is received in the opening 1500 of the insertion portion 1201, extends along the length of the insertion portion 1201, transitions into a passage 152 formed in the threaded portion 102T, and then passes laterally out of passage 152 to connect to a connector, an electronic panelboard or other like electronic component 154 including or coupled or configured to couple to a transmitter electronics of the transmitter and sensor assembly 115. Thus, upon insertion and then retraction of the insertion portion 1201 in and from the user's skin 113, the biosensor 150 can remain in place by being removed from passage 152 and the opening 1500.

Operation of biosensor inserter 100 is now described with reference to FIGS. 2A-2F and FIG. 3, which illustrates a flowchart of a method 300 of using a biosensor inserter 100 to insert a biosensor 150 in accordance with embodiments provided herein.

In operation, the transmitter and sensor assembly 115 (shown dotted in FIGS. 2A-2F) can be detachably coupled to the transmitter carrier 114 and may be positioned within the recess 118 in the lower region of transmitter carrier 114, in some embodiments. Transmitter and sensor assembly 115 includes an adhesive layer to adhere the transmitter and sensor assembly 115 to the user's skin 113 upon retraction of the insertion device 120. However, as should be apparent, a recess is optional, and the transmitter and sensor assembly 115 may be simply detachably mounted to the lower region of the transmitter carrier by any suitable means.

Figure 3:
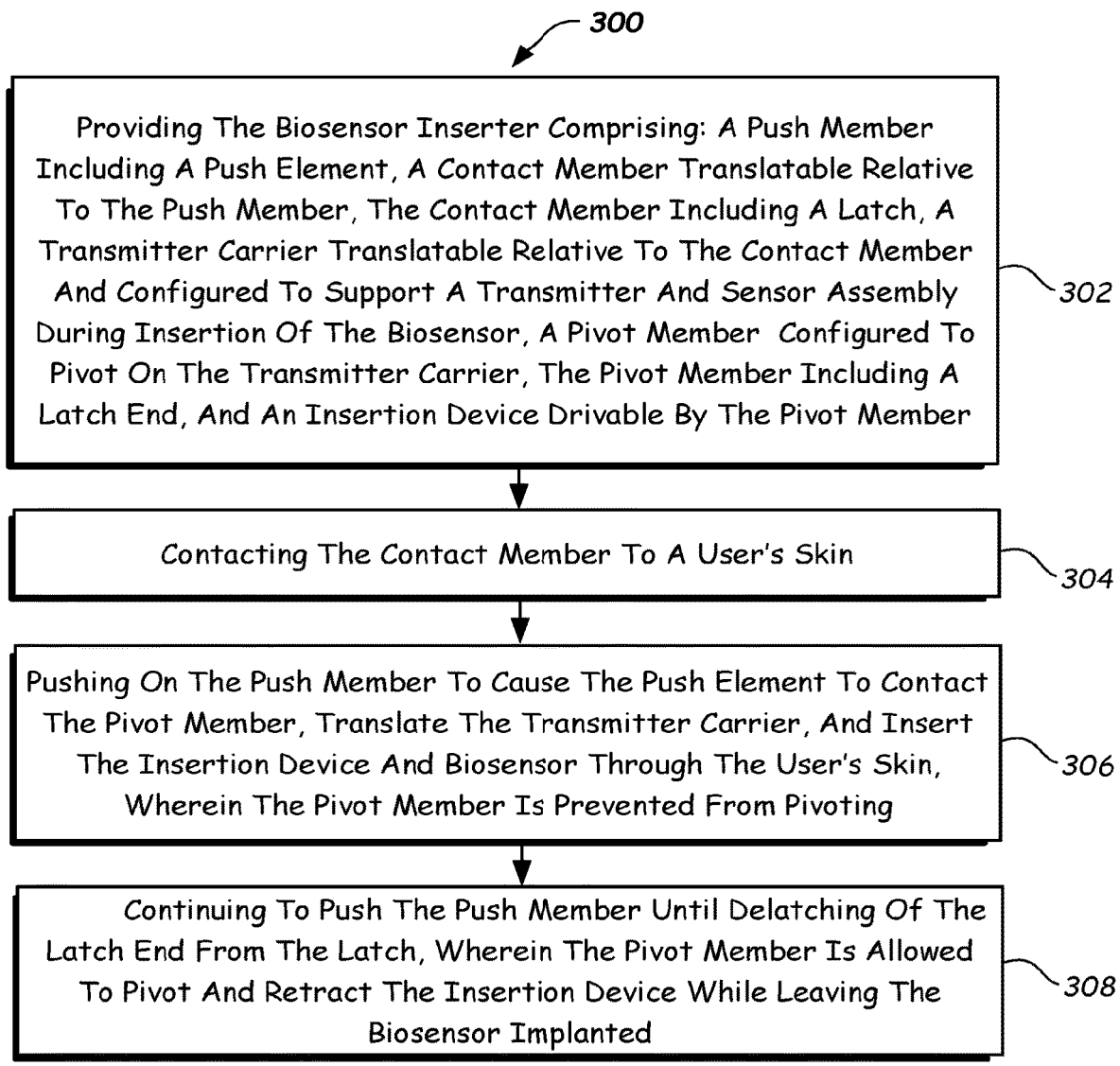
FIG. 3 illustrates a flowchart of a method of using a biosensor inserter to insert a biosensor in accordance with embodiments provided herein.

To begin the insertion method 300 of FIG. 3, the needle cover 124 is removed from insertion portion 1201 of insertion device 120 and the contact member 106 of the biosensor inserter 100 is placed in contact with the skin 113 surrounding an insertion site 110 of a user, such as on an upper arm, an abdomen region, or another suitable location to avoid insertion into muscle. This is shown in FIG. 2A.

To begin insertion, a force F is applied to the push member 102 by a user so as to cause the push member 102 to slide over the contact member 106 and move toward the insertion site 110. Movement of push member 102 over contact member 106 causes push element 104 to contact the push element interface feature 140 [See also FIGS. 1N-1P] of pivot member 116, which causes transmitter carrier 114 and pivot member 116 to translate and move toward the insertion site 110, as shown in FIG. 2B, with the latch end 117 moving linearly relative to and toward the latch 109 of contact member 106, while end 116E slides along guide feature 132.

Such axial movement is allowed after the applied force F is sufficient to cause first pre-insertion lock feature 142 (e.g., hook as shown in FIG. 1A) to flex inward, and out of pre-insertion lock feature 144 (e.g., slot or groove) of push member 102, according to the insertion method 300. During this first portion of the stroke of the insertion method 300, pivot member 116 is prevented from pivoting via contact of end 116E with the wall surface (e.g., inner guide groove 132) of the contact member 106, as transmitter carrier 114 and pivot member 116 translate toward the insertion site 110.

As shown in FIG. 2C, transmitter carrier 114 and pivot member 116 continue to move toward the insertion site 110 until insertion portion 1201 makes contact and enters insertion site 110, and a bottom surface of transmitter and sensor assembly 115 contacts the skin 113 around the insertion site 110. In some embodiments, bottom surface of transmitter and sensor assembly 115 may adhere (e.g., via an adhesive material) to the user's skin 113 surrounding the insertion site 110. The insertion portion 1201 and biosensor 150 enters the insertion site 110 where biosensor 150 can make contact with interstitial fluid in the subcutaneous region 113S. The biosensor 150 can be placed 4 mm to 6 mm into the skin 113, for example, although other depths may be used.

As shown in FIG. 2C, end 116E of pivot member 116 remains in contact with the inner surface (e.g., guide surface 132 of latch 109) of inner member 106 and is prevented from pivoting in the first portion of the stroke. Thus, during insertion of the biosensor 150, the pivot member 116 is prevented from pivoting. This causes insertion portion 1201 to remain in a fixed position relative to the pivot member 116 and transmitter carrier 114, with flange 120F against the top surface of the transmitter and sensor assembly 115.

Figure 2D:
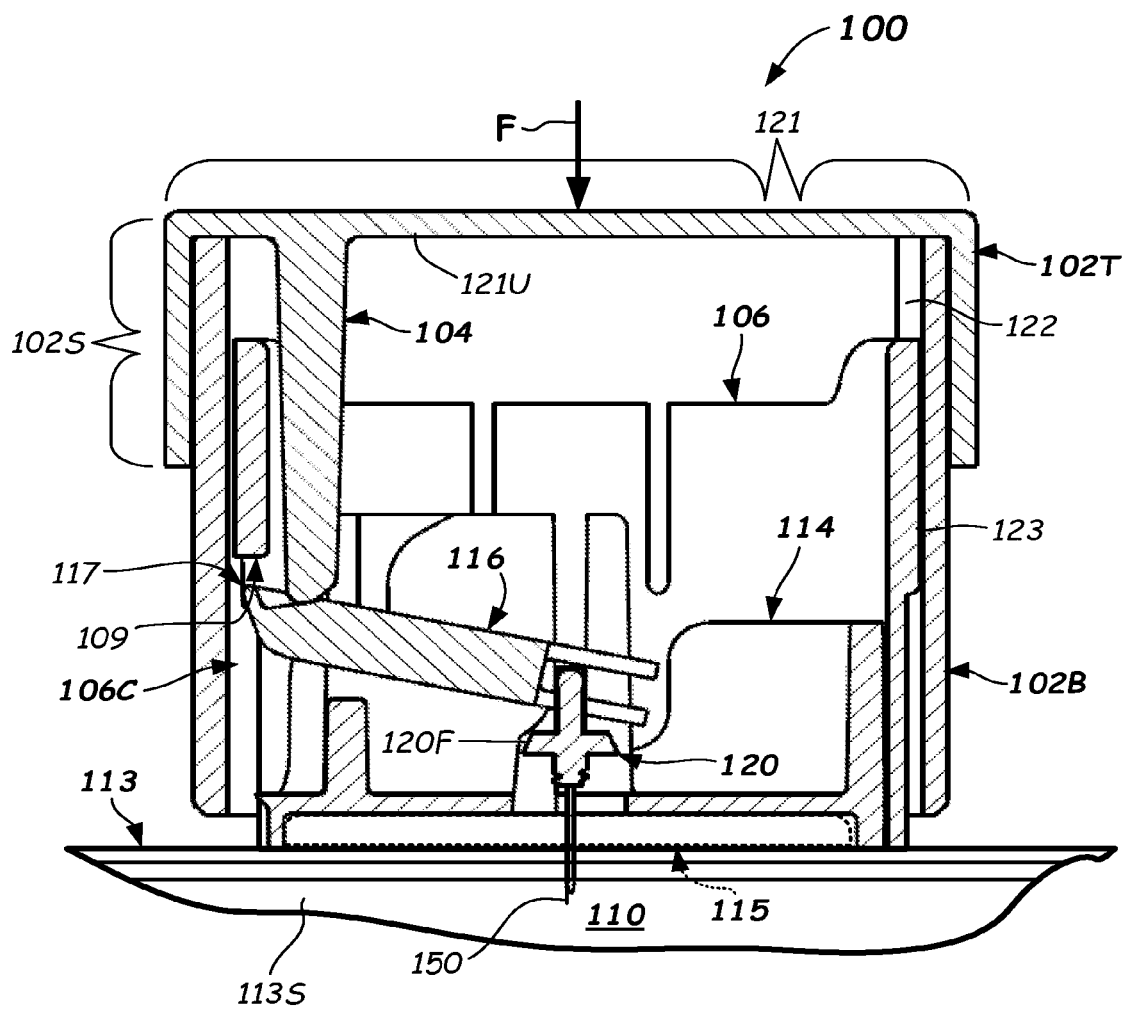
Figure 2E:
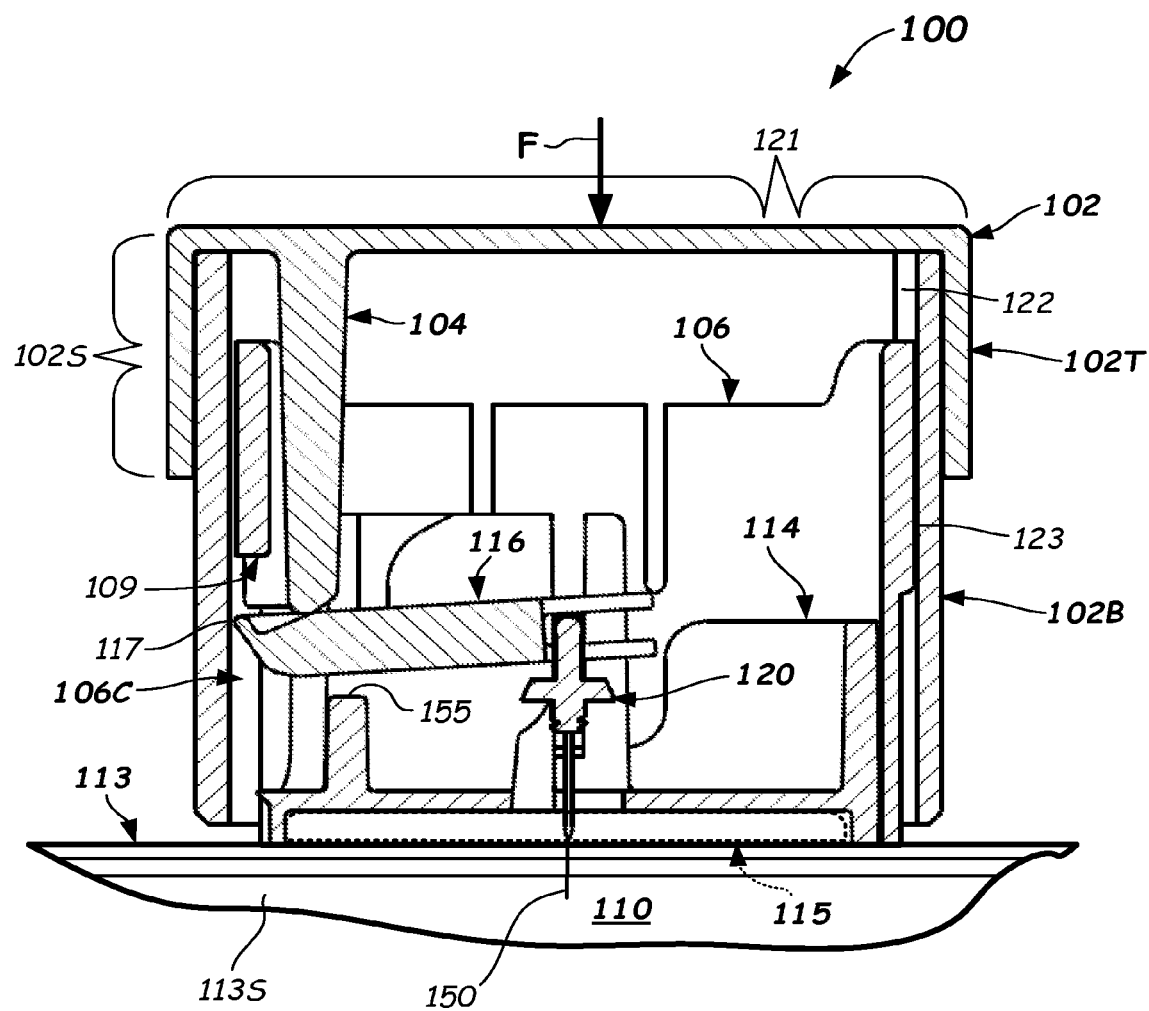

As shown in FIG. 2D, following insertion of the biosensor 150 (and/or adhesion of the transmitter and sensor assembly 115 to the skin 113 around the insertion site 110), the outer member 102 continues to move over the inner member 106 toward the insertion site 110 in a second portion of the stroke. When the latch end 117 of the pivot member 116 moves past the latch 109 at the start of the second portion of the stroke, the pivot member 116 is allowed to pivot via the pushing by push element 104, rotate under latch 109 and into cutout portion 106C. The pivoting causes the retraction of the insertion device 120 in the second portion of the stroke.

Figure 2F:
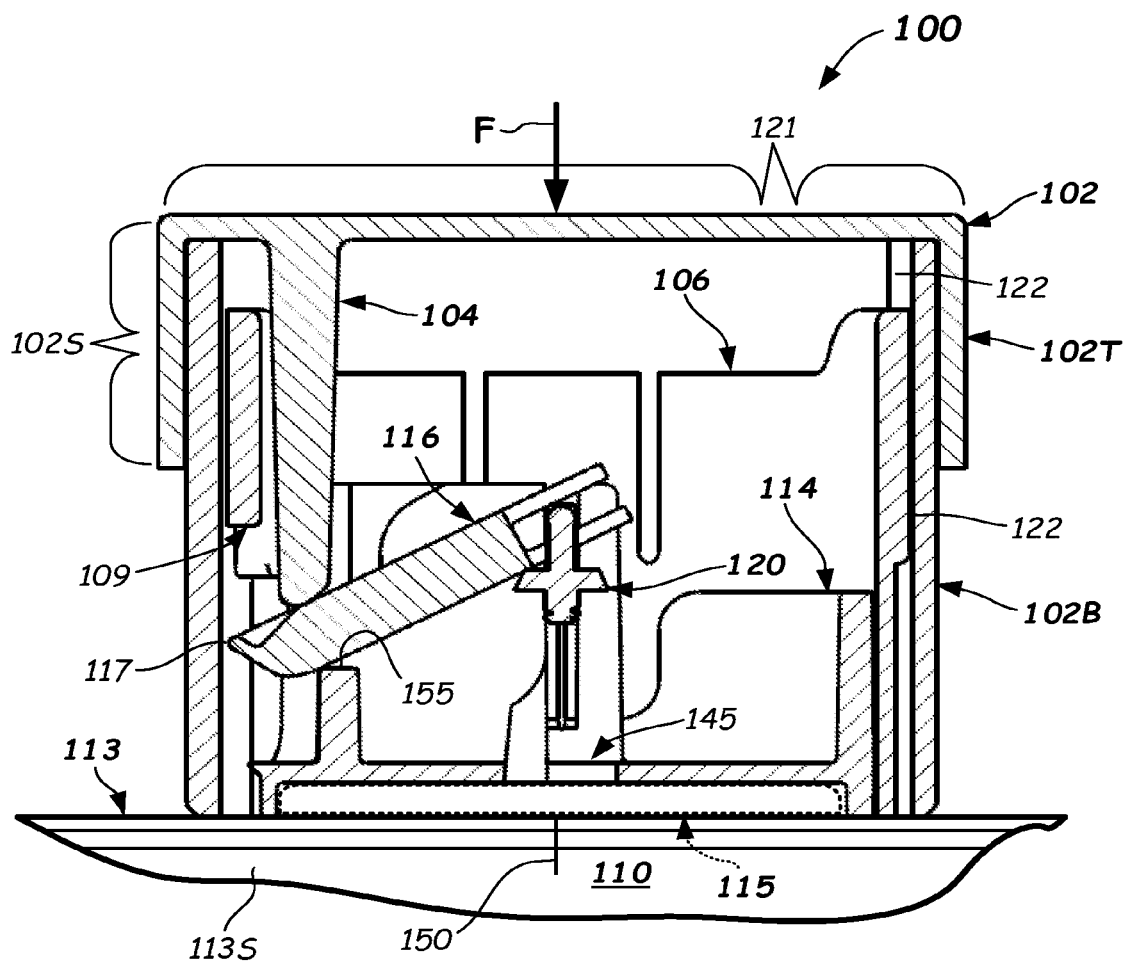

During the retraction, pivot member 116 pivots on the transmitter carrier 114 due to the force applied by push element 104 on pivot member 116 (as shown in FIG. 2D). As this occurs, insertion portion 1201 of insertion device 120 retracts from the insertion site 110 and flange 120F moves away from transmitter and sensor assembly 115. As the outer member 102 continues to move over the inner member 106 toward the insertion site 110, push element 104 continues to press against pivot member 116. Eventually, as shown in FIG. 2F, pivot member 116 pivots sufficiently for insertion device 120 to be completely removed from the user's skin 113 and leave the implanted biosensor 150 therein. As the push member 102 is pushed further, the insertion device 120 is retracted fully above the aperture 145. As such, insertion portion 1201 of insertion device 120 cannot inadvertently be reinserted into insertion site 110. Additionally, as push member 102 continues to move toward insertion site 110, after insertion, an axial stop feature 155 (FIG. 1J and FIG. 2F) of transmitter carrier 114 can contact pivot member 116 and prevent insertion device 120 from retracting further.

Biosensor inserter 100 then may be removed, leaving transmitter and sensor assembly 114 in place, with the bottom surface of transmitter and sensor assembly 115 adhered to the user's skin 113 at the insertion site 110 and biosensor 150 in contact with interstitial fluid (as shown in FIG. 2F). In some embodiments, in which the push member 102 and/or contact member 106 are formed of recyclable or biodegradable material, these components may be recycled or composted.

Referring now to FIG. 3, an embodiment of a method 300 of using a biosensor inserter (e.g., biosensor inserter 100) to insert a biosensor (biosensor 150) is described. The method 300 comprises, in block 302, providing the biosensor inserter 100 comprising: a push member (e.g., push member 102) including a push element (e.g., push element 104), a contact member (e.g., contact member 106) translatable relative to the push member, the contact member including a latch (e.g., latch 109), a transmitter carrier (e.g., transmitter carrier 114) translatable relative to the contact member and configured to support a transmitter and sensor assembly (e.g., transmitter and sensor assembly 115) during insertion of the biosensor (e.g., biosensor 150), a pivot member (e.g., pivot member 116) configured to pivot relative to the transmitter carrier, the pivot member including a latch end (e.g., latch end 117), and an insertion device 120 (insertion device 120) drivable by the pivot member.

The method 300 further comprises, in block 304, contacting the contact member (e.g., contact member 106) to a user's skin (e.g., skin 113 as shown in FIG. 2A). The contacting is followed by pushing, in block 306, on the push member 102 (e.g., push member 102) to cause the push element 104 to contact the pivot member 116 (e.g., at push element interface feature 140, such as a pocket), translate the transmitter carrier (e.g., axially translate the transmitter carrier 114 within the contact member 106), and insert the insertion device (e.g., the insertion portion 1201 of the insertion device 120) and biosensor 150 through the user's skin 113, wherein the pivot member (e.g., pivot member 116) is prevented from pivoting. In particular, pivot member (e.g., pivot member 116) is prevented from pivoting over a first portion of the stroke.

The method 300 further comprises, in block 308, continuing to push the push member (e.g., push member 102) until delatching of the latch end (e.g., latch end 117) from the latch (e.g., latch 109 of the contact member 106) occurs, wherein the pivot member 116 is allowed to pivot and retract the insertion device 120, while leaving the biosensor 150 implanted in the user's skin 113. Delatching occurs after the first portion of the stroke when the latch end 117, as a result of the pushing of pivot member 116 by push element 104, moves beyond the latch 109 and can rotate underneath the latch 109. The pivoting of the pivot member 116 in a second portion of the stroke of the push member 102 operatively retracts the insertion portion 1201 of the insertion device 120 from the user's skin 113 and leaves behind the implanted sensor 150.

Figure 4A:
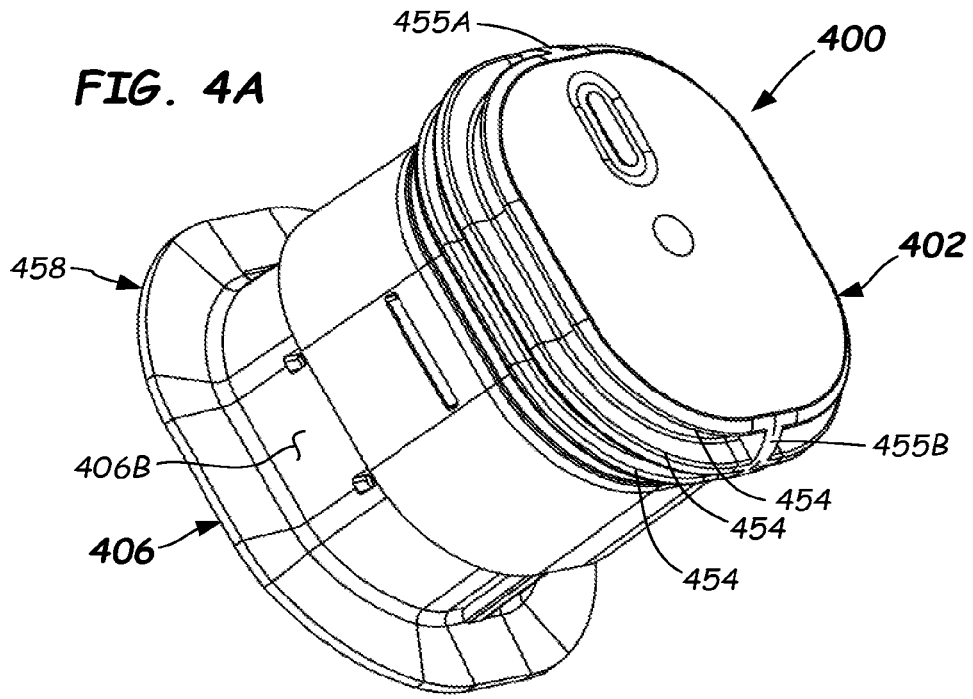
FIG. 4A is a top-perspective view of an alternative embodiment of biosensor inserter in accordance with the disclosure.
Figure 4B:
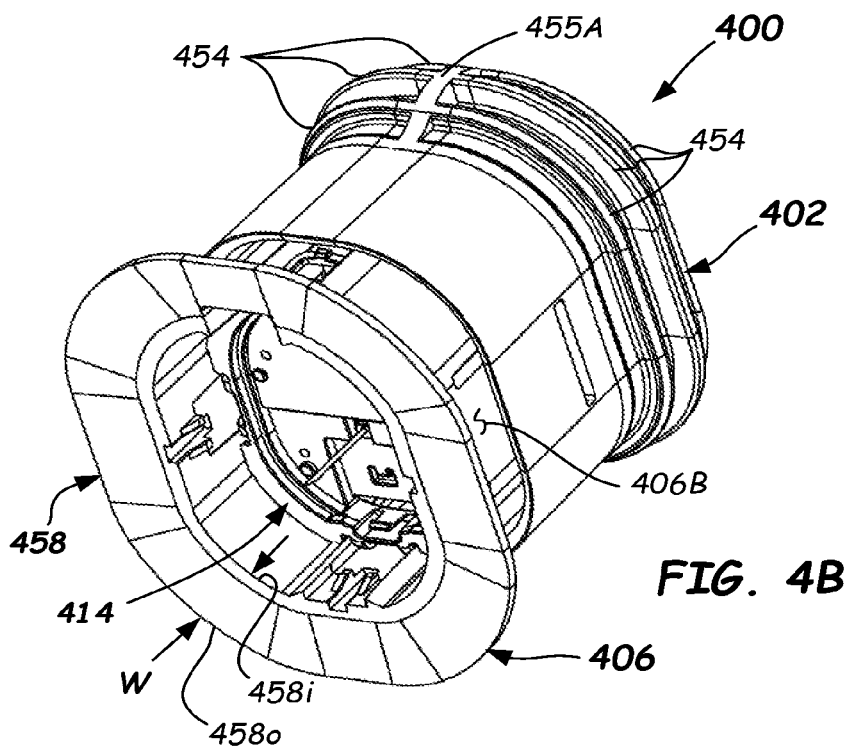
FIG. 4B is a bottom-perspective view of the biosensor inserter of FIG. 4A with the transmitter and biosensor assembly removed for illustration purposes in accordance with the disclosure.

FIGS. 4A and 4B illustrate an alternative embodiment of the biosensor inserter 400. This embodiment has several features that are advantaged ergonomically and/or functionally as compared to the previously-described embodiments herein. In particular, the overall shape, including the shape of the push member 402 and the contact member 406 are elongated in lateral cross-section as compared to the round shape of the embodiments of the biosensor inserter 100 shown in FIGS. 1A-1C. This elongated shape allows for a more ergonomically-secure grasp of the push member 402. Moreover, given that the transmitter and sensor assembly 115 (not shown in FIG. 4B) tends to be made up of rectangular circuitry components, an elongated shape can offer a more compact overall configuration. To further improve the ergonomic grasping of the push member 404, the insertion device 400 can comprise a plurality of ribs 454 that extend circumferentially around the upper perimeter of push member 402. As shown, ribs 454 can extend greater than 150 degrees around the top portion of the push member 402. Like ribs 454 are provided on the opposite side of the push member 402. As shown, three ribs are formed via molding on either side and extend circumferentially around the perimeter of the push member 402 and connect with end ribs 455A, 455B. The end ribs 455A, 455B can be aligned with the vertical direction as shown. The height of the ribs 454 may be different so to provide an arcuate vertical grasping profile as best shown being configured on end ribs 455A, 455B. The height of the ribs 454 may range from 1 mm to 3 mm for each rib 454, for example. The width of the ribs 454 may range from 1 mm to 5 mm, for example.

Figure 5A:
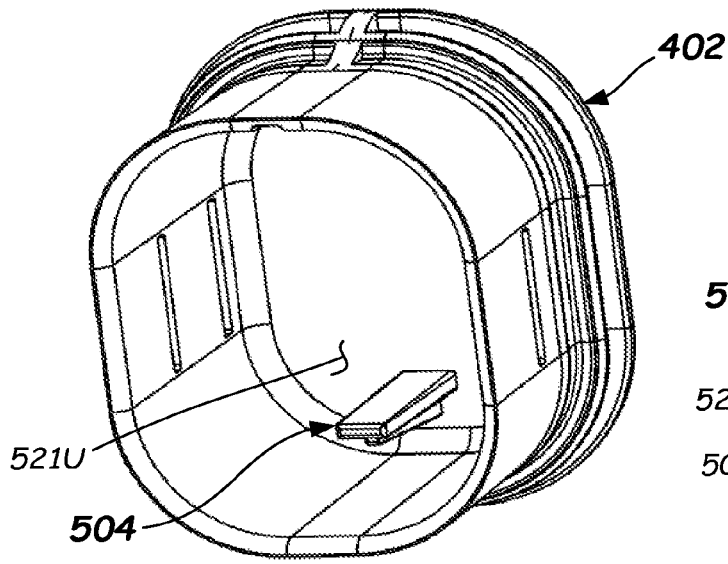
FIG. 5A is a bottom-perspective view of an alternative embodiment of push member and push element in accordance with one or more embodiments of the disclosure.
Figure 5B:
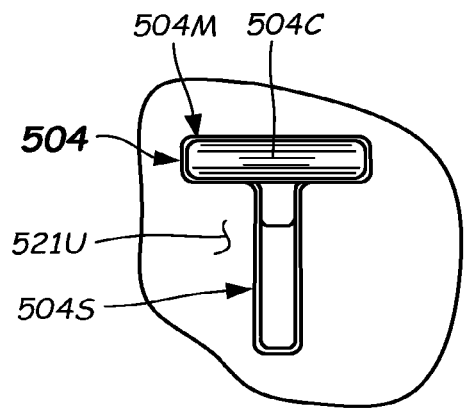
FIG. 5B is a partial plan view of an alternative embodiment of push element including a T-shaped cross section in accordance with the disclosure.
Figure 5C:
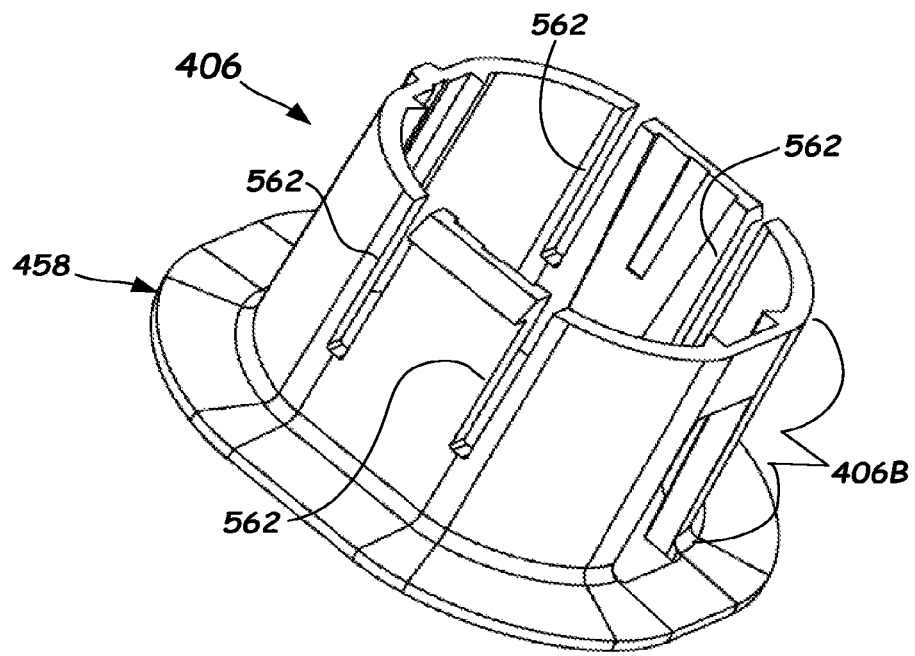
FIG. 5C is a front-perspective view of an alternate embodiment of contact member including a flange and fin supports in accordance with the disclosure.

Now referring to FIGS. 4A-4B and 5C, an alternate embodiment of a contact member 406 is provided that can include a peripheral flange 458. The peripheral flange 458 can extend outwardly from some or all of a body portion 406B of the contact member 406. As best shown in FIG. 4B, the peripheral flange 458 can extend outwardly by a width W measured along a plane of the flange 458 from an inner edge 458i to an outer edge 458O. Width W can be greater than or equal to 5 mm at least partway around the periphery, wherein W is a width of the peripheral flange 458. In some embodiments, the peripheral flange 458 may extend fully around the circumferential periphery, and may have a width W greater than or equal to 5 mm at all locations. The inner edge 458i may include some recesses and protuberances for engaging with the transmitter carrier 414. In some embodiments, the contact member 406 with the peripheral flange 458 can have Ac 500 $mm^2$, wherein Ac is a contact area of the peripheral flange 458 that is configured to contact a user's skin during insertion of the biosensor.

Referring now to FIGS. 5A and 5B, the push element 504 extending from the underside 521U of the push member 402 can include a T-shaped cross section along at least a portion of its length as best shown in FIG. 5B to provide enhanced rigidity yet a thinner profile for less molding issues. The push element 504 can include a main portion 504M including a contact end 504C that may include a cylindrical end configuration that contacts a push element interface feature (e.g., a pocket 640 of pivot member 616 as shown in FIG. 6B, for example). Push member 402 can also include support portion 504S, which coupled to the main portion 504M, such as at a right angle thereto to form the T-shaped cross section. Support portion 504S may be somewhat shorter than the main portion 504M so that the contact end 504C does not impede rotation in the pocket 640 as the pivot member 616 rotates. Push member 402 may include draft angles on all surfaces to allow for improved removal from the mold.

Figure 6A:
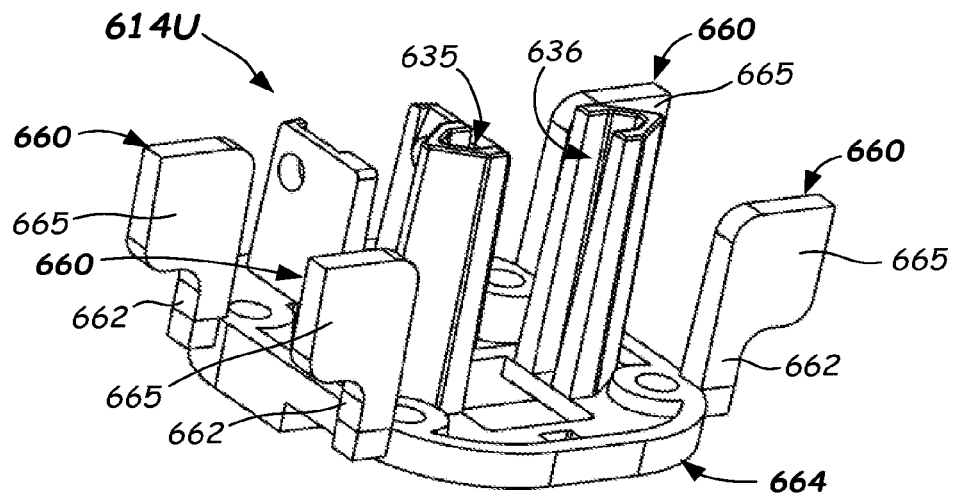
FIG. 6A is a front-perspective view of a portion of an alternative embodiment of transmitter carrier including fins and closed guides in accordance with the disclosure.
Figure 6B:
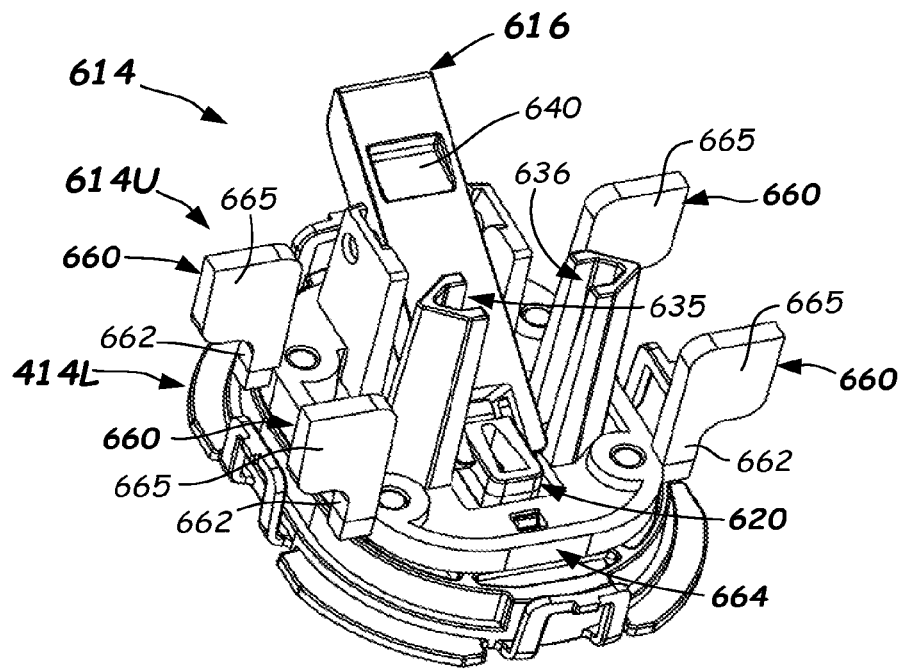
FIG. 6B is a front-perspective view of an alternative two-piece transmitter carrier in accordance with the disclosure.

Now referring to FIGS. 6A-6B, an alternative embodiment of a transmitter carrier 614 is shown that comprises a plurality of fins 660 configured to be received and slide within vertical slots 562 formed in the contact member 406. As shown, there are four of the fins 660. Respective pairs of the fins 660 can lie in a same vertical plane. Each of the fins 660 is made up of a vertical connector 662 extending from a base 664. Each of the vertical connectors 662 connects to a paddle 665 that extends upwardly and laterally outward from the connector 662, wherein the outermost part of the paddles 665 are received in and register within the vertical slots 562.

Figures 6C, 6D:
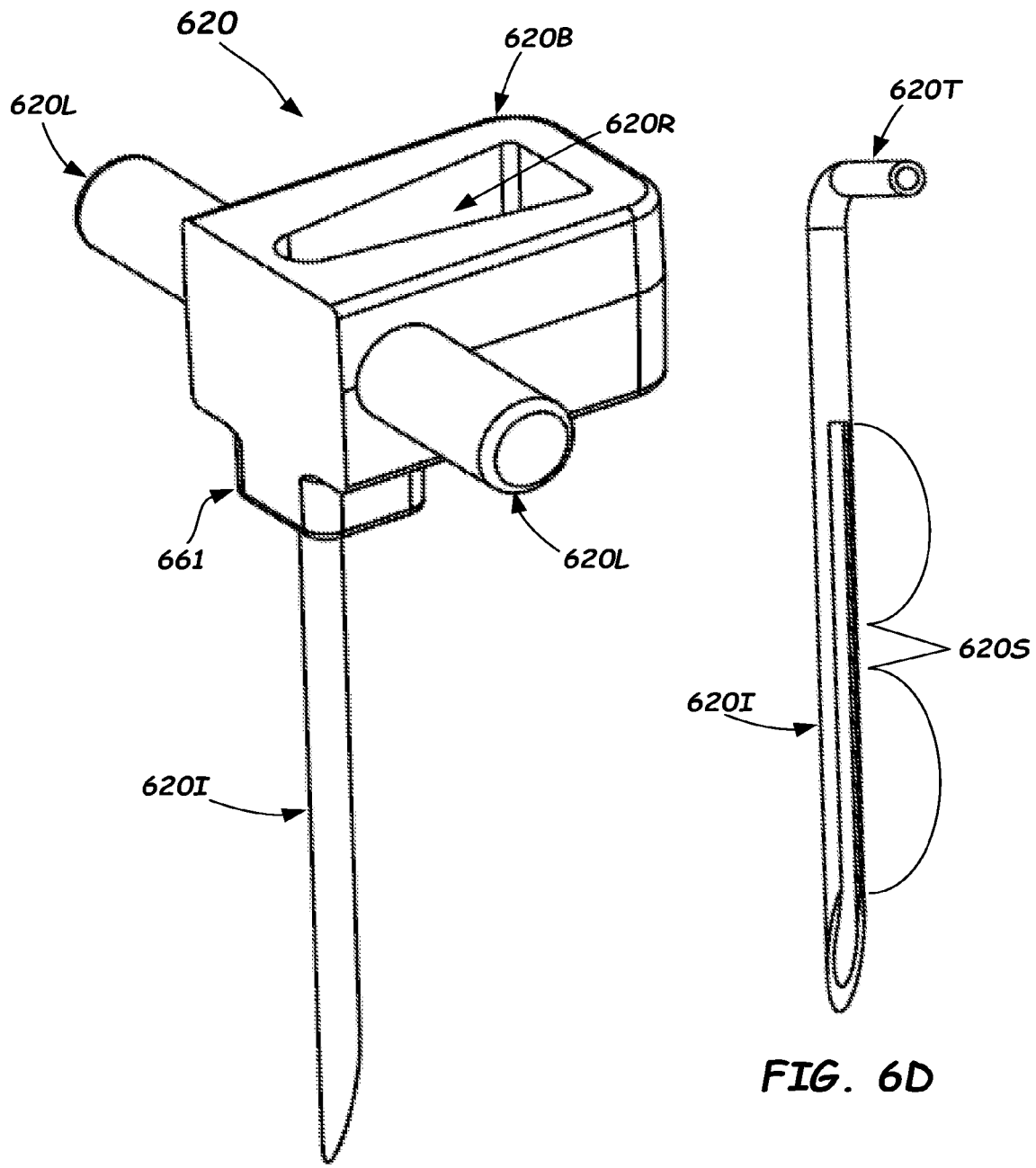
FIGS. 6C and 6D are front-perspective views of an embodiment of an inserter device and an insertion needle, respectively, in accordance with the disclosure.

Further, in the depicted embodiment of FIGS. 6A-6B, the transmitter carrier 614 comprises closed guide grooves 635, 636 configured to receive legs 620L of the insertion device 620 as shown in FIGS. 6C and 6D. The closed guide grooves 635, 636 include open portions facing each other and the groves extend vertically as shown and have a shape that guides the insertion device 620 during both insertion and retraction. Each of the closed guide groves 635, 636 have a closed portion opposite the open portion and positioned adjacent to the ends of the legs 620L of the insertion device 620.

As shown in FIGS. 6C and 6D, the insertion device 620 includes a main body 620B made of a polymer material, such as, but not limited to, acrylonitrile butadiene styrene (ABS), polycarbonate, nylon, acetal, polyphthalamide (PPA), polysulfone, polyethersulfone, polyetheretherketone (peek), polypropylene, high-density polyethylene (HDPE), and low-density polyethelene (LDPE), and an insertion needle 6601, which may be stainless steel or the like. Other suitable material could be used. Main body 620B includes legs 620L extending from lateral sides, wherein the legs 620L are received in the closed guide grooves 635, 636 (FIGS. 6A-6B). Main body 620B includes recess 620R that is sized to receive a transverse portion 620T of the insertion needle 6601, and a hole (not shown) through registration portion 661 that receives the sensor carrying portion 620S there through. Once inserted, an adhesive or potting compound can be used to secure the transverse portion 620T of the insertion needle 6201 into the recess 620R, and thus secure the insertion needle 6201 to the main body 620B.

FIG. 7 illustrates an exploded view of the various components of the biosensor inserter 400. As shown, are the push member 402 that is configured to be securely grasped by the user, the pivot member 416, which pivots to accomplish retraction of the insertion device 620 after insertion of the biosensor, the first and second parts of the transmitter carrier 414A, 414B, the insertion device 620, and the contact member 406 with laterally-extending peripheral flange 458.

The foregoing description discloses only example embodiments. Modifications of the above-disclosed apparatus and methods, which fall within the scope of this disclosure, will be readily apparent to those of ordinary skill in the art.

What is claimed is:

1. A biosensor inserter, comprising:
  a push member receiving a contact member therein, the contact member being translatable relative to the push member, the contact member configured to translate within the push member upon a force exerted on the push member;
  a pivot member comprising a latch end and an injection device support end opposite of the latch end, the latch end arranged to engage the push member; and
  an insertion device comprising a body portion and an insertion portion, the body portion including at least one leg arranged to engage a fork disposed at the injection device support end of the pivot member, wherein the insertion device is drivable by the pivot member to insert a biosensor via the insertion portion.

2. The biosensor inserter of claim 1, further comprising:
  a transmitter carrier supporting a transmitter and sensor assembly of the biosensor inserter, the transmitter carrier being translatable relative to the contact member.

3. The biosensor inserter of claim 2, further comprising:
  at least one side support extending from the transmitter carrier and configured to engage the body portion of the insertion device.

4. The biosensor inserter of claim 3, wherein the at least one side support includes a guide adapted to receive the at least one leg therein.

5. The biosensor inserter of claim 4, wherein the pivot member is rotatably coupled to the at least one side support.

6. The biosensor inserter of claim 5, further comprising:
a latch extending from an inner side of the contact member and engaging the latch end of the pivot member.

7. The biosensor inserter of claim 6, further comprising:
a first pre-insertion lock disposed at the push member; and
a second pre-insertion lock disposed at the contact member,
wherein the first pre-insertion lock engages the second pre-insertion lock prior to the force being exerted on the push member.

8. A biosensor inserter configured to insert a biosensor, comprising:
a push member including a push element;
a contact member translatable relative to the push member, the contact member including a latch;
a transmitter carrier translatable relative to the contact member and arranged to support a transmitter and sensor assembly of the biosensor inserter;
a pivot member coupled to the transmitter carrier at a laterally-extending member and configured to rotate therearound, the pivot member including a latch end arranged to engage the push element and the latch; and
an insertion device drivable by the pivot member to insert the biosensor,
wherein the insertion device comprises a body portion, and wherein the body portion comprises at least one leg engaging and contacting the pivot member,
wherein during insertion of the biosensor in a first portion of a stroke, the pivot member is prevented from rotating via the latch, and
wherein during insertion of the biosensor in a second portion of the stroke, the pivot member translates past the latch, thereby allowing the pivot member to rotate about the laterally-extending member and retract the insertion device.

9. The biosensor inserter of claim 8, further comprising:
an internal guide disposed at the latch,
wherein the internal guide is configured to interface with the latch end of the pivot member.

10. The biosensor inserter of claim 8, further comprising:
one or more side supports extending from the transmitter carrier,
wherein each of the one or more side supports comprises a guide configured to interface with the insertion device and prevent rotation of the insertion device during insertion of the biosensor.

11. The biosensor inserter of claim 10, wherein the pivot member rotatably couples to each side support of the one or more side supports of the transmitter carrier.

12. The biosensor inserter of claim 8, further comprising:
an axial stop protrusion extending from the transmitter carrier and arranged to contact the pivot member during the second portion of the stroke.

13. The biosensor inserter of claim 8, wherein the pivot member further comprises a push element interface surface adapted to engage the push element during the first portion of the stroke.

14. The biosensor inserter of claim 8, further comprising:
a first alignment guide disposed at the push member; and
a second alignment guide disposed at the contact member,
wherein the first alignment guide engages the second alignment guide, and
wherein engagement of the first alignment guide and the second alignment guide prevents rotation of the contact member relative to the push member.

15. The biosensor inserter of claim 8, wherein the pivot member further comprises an injection device support end opposite the latch end, and wherein the injection device support end comprises a fork configured to receive the at least one leg of the insertion device.

16. A biosensor inserter configured to insert a biosensor, comprising:
a transmitter carrier arranged to support a transmitter and sensor assembly of the biosensor inserter;
a contact member configured to translate in an axial direction in relation to the transmitter carrier, the contact member including a latch extending a length in the axial direction;
a pivot member rotatably attached to the transmitter carrier, the pivot member including a latch end engaging the latch and an injection device support end; and
an insertion device comprising a body portion and an insertion portion, the body portion including legs configured to engage a fork disposed at the injection device support end of the pivot member,
wherein during insertion of the biosensor in a first portion of a stroke, the contact member translates in the axial direction, thereby translating the latch end of the pivot member along the length of the latch, the latch preventing rotation of the pivot member, and
wherein during insertion of the biosensor in a second portion of the stroke, the latch end translates a distance greater than the length of the latch, thereby allowing rotation of the pivot member and retraction of the insertion portion of the insertion device.

17. The biosensor inserter of claim 16, further comprising:
a push member receiving the contact member therein, the contact member configured to translate in the axial direction in relation to the push member.

18. The biosensor inserter of claim 16, further comprising:
an axial stop protrusion extending axially from the transmitter carrier and arranged to contact the pivot member during the second portion of the stroke.

19. The biosensor inserter of claim 16, further comprising:
a push member including a push element arranged to interface with the latch end of the pivot member,
wherein the push element is arranged to drive the pivot member during the first portion of the stroke and during the second portion of the stroke.

20. The biosensor inserter of claim 16, wherein the transmitter carrier comprises at least one fin received within at least one vertical slot formed in the contact member.

* * * * *